US007122367B2

(12) United States Patent
Milcamps et al.

(10) Patent No.: US 7,122,367 B2
(45) Date of Patent: Oct. 17, 2006

(54) DIACYLGLYCEROL ACYLTRANSFERASE GENES, PROTEINS, AND USES THEREOF

(75) Inventors: Anne Milcamps, Gavirate (IT); David A. Pan, Scotland (GB); Michael R. Pollard, Okemos, MI (US)

(73) Assignee: Board of Trustees Operating Michigan State University, East Lansing, MI (US)

( * ) Notice: Subject to any disclaimer, the term of this patent is extended or adjusted under 35 U.S.C. 154(b) by 0 days.

(21) Appl. No.: 10/859,247

(22) Filed: Jun. 2, 2004

(65) Prior Publication Data

US 2005/0130284 A1 Jun. 16, 2005

Related U.S. Application Data

(60) Provisional application No. 60/475,371, filed on Jun. 3, 2003.

(51) Int. Cl.

| | |
|---|---|
| ***C12N 1/20*** | (2006.01) |
| ***C12N 9/12*** | (2006.01) |
| ***C12N 1/00*** | (2006.01) |
| ***C12N 5/08*** | (2006.01) |
| ***C07H 21/02*** | (2006.01) |
| ***C07H 21/04*** | (2006.01) |

(52) U.S. Cl. ................. 435/252.3; 536/23.1; 536/23.2; 435/194; 435/410; 435/243; 435/320.1

(58) Field of Classification Search ................ 435/252, 435/193; 535/232; 800/295
See application file for complete search history.

(56) References Cited

FOREIGN PATENT DOCUMENTS

| | | |
|---|---|---|
| WO | WO 00/36114 | 6/2000 |
| WO | WO 00/32756 | 8/2000 |

OTHER PUBLICATIONS

Hobbs et al. (1999) FEBS Lett. 452: 145-149.
Bouvier-Nave et al. (2000) Eur. J. Biochem. 267: 85-96.
Routaboul et al. (1999) Plant Physiol. Biochem. 37: 831-840.
Zou et al. (1999) Plant J. 19: 645-653.
Jako et al. (2001), Plant Phys 126, 861-874.
Lin et al. (1999) J. Biol. Chem. 274:23276-23285.
Bus et al., Chemistry and Physics of Lipids, 16:123-132 (1976).
Fretzen, FETT—LIPID 100:161-166 (1998).

*Primary Examiner*—Rebecca Prouty
*Assistant Examiner*—Mohammad Meah
(74) *Attorney, Agent, or Firm*—Medlen & Carroll, LLP

(57) ABSTRACT

The present invention relates to diacylglycerol acyltransferase genes and proteins, and methods of their use. In particular, the invention describes genes and proteins that exhibit both long-chain acyltransferase and acetyltransferase activity. The present invention encompasses both native and recombinant wild-type forms of the transferase, as well as mutants and variant forms, some of which possess altered characteristics relative to the wild-type transferase. The present invention also relates to methods of using diacylglycerol acyltransferase genes and proteins, including in their expression in transgenic organisms and in the production of acetyl-glycerides in plant oils, and in particular seed oils.

13 Claims, 7 Drawing Sheets

FIG. 5

```
1       atggctgcta acttgaacga agcctcggat cttaattttt cgcttcggag gagaactggt
61      ggcatctcaa gtacgactgt gcctgattct agttccgaga caagttcgtc ggaggcggac
121     tatttggacg gaggcaaagg tgccgcggac gtcaaagatc gtggggatgg tgcggtggag
181     tttcagaatt cgatgaagaa cgtggagagg attgagaaac atgagagccg agtaggattg
241     gattcgagat tcacgtatag gccatcggtc ccggctcatc gcacaataaa ggagagcccg
301     cttagctcgg acgcaatatt caaacagagt cacgcaggtc tcttcaatct ctgtatagta
361     gttctggttg ctgtgaacag caggctgatc attgaaaatc taatgaagta tggatggtta
421     ataaggagtg ggttttggtt cagctcaaga tcattgagag actggcccct ttttatgtgt
481     tgtctcacac taccagtatt ccctcttgct gcttttctgt ttgagaagtt ggctcaaaaa
541     aatttaatat ctgaacctgt tgttgttttg cttcatatag taaacactac agctgccgtt
601     ttataccctg ttttggtgat tctaaggtgt gattctgcct ttatgtctgg ggttacgttg
661     atgctctttg cttgtattgt gtggttaaag ttggtatctt atgctcatac caactatgat
721     atgagagccc tcaccaagtc tgttgaaaag ggggacacgc cgttgagctc tcagaacatg
781     gattactcgt ttgatgtcaa tatcaagagt ttggcatatt ttatggttgc tcccacatta
841     tgttaccaga ttagctatcc tcgtacccca tatgttcgca agggttgggt ggttcgtcaa
901     tttgtcaagt taataatatt tactggactt atgggattta taattgaaca atatatcaat
961     cctattgtcc agaattcaca acaccctttg aaaggaaact ttttgtatgc cattgagaga
1021    gttttgaagc tttcagtccc aaacctttat gtttggctct gcatgttcta ctgccttttt
1081    catctctggt taaacatact tgctgaactt ctttgttttg gtgatcgtga gttctacaag
1141    gattggtgga acgctaaaac tgttgaggag tactggagaa tgtggaacat gcctgttcat
1201    aagtggatgg ttcgtcatat ctacttccca tgcttgagga acgggatacc caagggtgtt
1261    gcttttgtca tttccttctt agtttctgcc gtcttccatg agctatgcat tgctgttccc
1321    tgccacatct tcaagttatg ggctttcttt ggaataatgc ttcaggttcc cttggtgttg
1381    atcacaagtt atctgcaaaa taagttcaga agctcaatgg tgggaaatat gatgttttgg
1441    ttctctttct gcattttttgg tcaacctatg tgcttacttc tatattacca tgatttgatg
1501    aatcgcaatg ggaagatgga gtag
```

FIG. 6

MANNLNEASD LNFSLRRRTG GISSTTVPDS SSETSSSEAD YLDGGKGAAD VKDRGDGAVE
FQNSMKNVER IEKHESRVGL DSRFTYRPSV PAHRTIKESP LSSDAIFKQS HAGLFNLCIV
VLVAVNSRLI IENLMKYGWL IRSGFWFSSR SLRDWPLFMC CLTLPVFPLA AFLFEKLAQK
NLISEPVVVL LHIVNTTAAV LYPVLVILRC DSAFMSGVTL MLFACIVWLK LVSYAHTNYD
MRALTKSVEK GDTPLSSQNM DYSFDVNIKS LAYFMVAPTL CYQISYPRTP YVRKGWVVRQ
FVKLIIFTGL MGFIIEQYIN PIVQNSQHPL KGNFLYAIER VLKLSVPNLY VWLCMFYCLF
HLWLNILAEL LCFGDREFYK DWWNAKTVEE YWRMWNMPVH KWMVRHIYFP CLRNGIPKGV
AFVISFLVSA VFHELCIAVP CHIFKLWAFF GIMLQVPLVL ITSYLQNKFR SSMVGNMMFW
FSFCIFGQPM CLLLYYHDLM NRNGKME

FIG. 7

```
Dagat E.a.   (1) -----------------MAANLNEASDLNFSLRR--------RTG-GISSTTVPDSSSETSSSEA
Dagat A.t.   (1) ---MAILDSAGVTTVTENGGGEFVDLDRLRRRKSR-----SDSSNGLLLSGSDNNSPSDDVGAPA
Dagat N.t.   (1) MVIMELPESVEMTTTTTTSGIENLNSDLNHSVRR------RRGSNGFEAASAINSSDANMSEDRR
Dagat P.f.   (1) MAILDSPEILDTTSSSADNGAAHHTTLRRRQSARSVPPLLDSDSNSLEAESAINDSENVRNDANL

                 66                                                            130
Dagat E.a.  (40) DYLDGGKGAADVKDRGDGAVEFQNSMKNVER------IEKHESRVG---LDSRFTYRPSVPAHRT
Dagat A.t.  (58) DVRDRIDSVVNDDAQGTANLAGDNNGGGDNN------GGGRGGGEGRGNADATFTYRPSVPAHRR
Dagat N.t.  (60) DVCGSGAGLETVNERSKSVGESSDVIRKEDDRNDNVANGEESKSTETTTTPFKFAYRASAPAHRR
Dagat P.f.  (66) IENLRGGAVESENEKQESYGKEEGAKVKE--------NGETSNGNGTDVMAVKFTFRPAAPAHRK

                 131                                                           195
Dagat E.a.  (96) IKESPLSSDAIFKQSHAGLFNLCIVVLVAVNSRLIIENLMKYGWLIRSGFWFSSRSLRDWPLFMC
Dagat A.t. (117) ARESPLSSDAIFKQSHAGLFNLCVVVLIAVNSRLIIENLMKYGWLIRTDFWFSSRSLRDWPLFMC
Dagat N.t. (125) IKESPLSSDAIFKQSHAGLFNLCVVVLIAVNSRLIIENLMKYGLLIRAGFWFSSKSLRDWPLLMC
Dagat P.f. (123) NKESPLSSDAIFKQSHAGLFNLCIVVLVAVNSRLIIENLMKYGWLIKSGFWFSSTSLRDWPLLMC
                  _____________________             ______
                          (1)                         (2)

                 196                                                           260
Dagat E.a. (161) CLTLPVFPLAAFLFEKLAQKNLISEPVVVLLHIVNTTAAVLYPVLVILRCDSAFMSGVTLMLFAC
Dagat A.t. (182) CISLSIFPLAAFTVEKLVLQKYISEPVVIFLHIIITMTEVLYPVYVTLRCDSAFLSGVTLMLLTC
Dagat N.t. (190) CLSLQILPLAAFLVEKLAQQRHLTERAVVTLHITITTAAILYPVLVILGCDSAFLFGVILMLVAC
Dagat P.f. (188) CLSLPVFALASFLVEKLVKLNYIPEWVAVFLHVTITTVEILFPVVVILRCDSAVLSGVTLMLFAC

                 261                                                           325
Dagat E.a. (226) IVWLKLVSYAHTNYDMRALTKSVEKGDTPLSSQNMDYSFDVNIKSLAYFMVAPTLCYQISYPRTP
Dagat A.t. (247) IVWLKLVSYAHTSYDIRSLANAADKANPEVS-----Y--YVSLKSLAYFMVAPTLCYQPSYPRSA
Dagat N.t. (255) IVWMKLVSYAHTNHDMRQLAKSTDKDETS----DGDFSYDVSFKSLAYFMVAPTLCYQLSYPHTP
Dagat P.f. (253) TVWLKLVSYAHTNYDLRVLAKSLDKWEAMSRYWNLDYAYDVSFKSLAYFMVAPTLCYQPSYPRTA

                 326                                                           390
Dagat E.a. (291) YVRKGWVVRQFVKLIIFTGLMGFIIEQYINPIVQNSQHPLKGNFLYAIERVLKLSVPNLYVWLCM
Dagat A.t. (305) CIRKGWVARQFAKLVIFTGFMGFIIEQYINPIVRNSKHPLKGDLLYAIERVLKLSVPNLYVWLCM
Dagat N.t. (316) CIRKGWVARQFIKLVIFTGLMGFIIEQYINPIVQNSQHPLKGNLLYAIERVLKLSVPNLYVWLCM
Dagat P.f. (318) CIRKGWVVRQLIKLVIFTGLMGFIIEQYINPIVQNSQHPLKGNLLYAIERVLKLSVPNLYVWLCM

                 391                                                           455
Dagat E.a. (356) FYCLFHLWLNILAELLCFGDREFYKDWWNAKTVEEYWRMWNMPVHKWMVRHIYFPCLRNGIPKGV
Dagat A.t. (370) FYCFFHLWLNILAELLCFGDREFYKDWWNAKSVGDYWRMWNMPVHKWMVRHIYFPCLRSKIPKTL
Dagat N.t. (381) FYCFFHLWLNILAELLCFGDREFYKDWWNAKTIDEYWRMWNMPVHKWMVRHIYFPCLRNGIPKGV
Dagat P.f. (383) FYCFFHLWLNILAELLCFGDREFYKDWWNARTVEEYWRMWNMPVHKWMVRHIYCPCLQNGIPKIV

                 456                                                           520
Dagat E.a. (421) AFVISFLVSAVFHELCIAVPCHIFKLWAFFGIMLQVPLVLITSYLQNKFRSSMVGNMMFWFSFCI
Dagat A.t. (435) AIIIAFLVSAVFHELCIAVPCRLFKLWAFLGIMFQVPLVFITNYLQERFG-STVGNMIFWFIFCI
Dagat N.t. (446) AILIAFLVSAVFHELCIAVPCRLFKWWAFMGIMFQVPLVILTNFLQNKFQSSMVGNMMFWCFFCI
Dagat P.f. (448) AVLIAFLVSAIFHELCVAVPCQIFKFWAFSGIMLQVPLVIVTNYLQEKFKNSMVGNMMFWCFFCI

                 521                  542
Dagat E.a. (486) FGQPMCLLLYYHDLMNRNGKME
Dagat A.t. (499) FGQPMCVLLYYHDLMNRKGSMS
Dagat N.t. (511) LGQPMCVLLYYHDVMNRKSSAR
Dagat P.f. (513) FGQPMCVLLYYHDLMNRKASAR
```

DIACYLGLYCEROL ACYLTRANSFERASE GENES, PROTEINS, AND USES THEREOF

This application claims priority to provisional patent application Ser. No. 60/475,371, filed Jun. 3, 2003, which is herein incorporated by reference in its entirety.

The present application was funded in part with government support under grant number 98-35503-6362 from the USDA-CSREES. The government may have certain rights in this invention.

FIELD OF THE INVENTION

The present invention relates to isolated diacylglycerol acetyltransferase (AcDAGAT) genes and polypeptides, and in particular *Euonymus* and *Euonymus*-like AcDAGAT genes and polypeptides where the enzyme exhibits an increased specificity for acetyl-CoA. The present invention also provides compositions comprising unique triacylglycerols synthesized by an AcDAGAT enzyme. The present invention also provides methods for using diacylglycerol acetyltransferase genes and polypeptides.

BACKGROUND OF THE INVENTION

Vegetable oils are utilized not only in the food industry, but also increasingly in the chemical industry. The utility of any particular oil depends upon chemical and physicochemical properties of the oil, which are determined by the composition of the constituent fatty acids. Plant oils are often modified to meet industry specifications. Such modification of vegetable oil has typically been achieved by chemical means (fractionation, interesterification, hydrogenation, or other chemical derivatization), but genetic means (plant breeding, mutagenesis and genetic engineering) are increasingly being used to provide novel oil feedstocks.

One class of particular interest is the class of triacylglycerols containing sn-3-acetyl glycerides (1,2-diacyl-3-acetins). These unusual triacylglycerols have an acetyl group at their sn-3 position. The occurrence and structural characterization of sn-3-acetyl glycerides in seed oils was first reported by Kleiman et al. (1967) (Lipids 2:473–478). Unlike most triacylglycerols, sn-3-acetyl glycerides exhibit strong optical activity. They are found at high levels in *Euonymus* species, representing up to 98% of the total triacylglycerols in the seed oil, and are also found in varying amounts in some other plant species. In the *Euonymus* sn-3-acetyl glycerides, the sn-1 and sn-2 positions are esterified with common long-chain fatty acids, predominantly palmitate, oleate and linoleate.

Currently, there are no commercial sources of oils rich in sn-3-acetyl glycerides. Moreover, plants with high levels of sn-3-acetyl glycerides are not grown commercially. In fact, the biosynthesis of these novel glycerides has only recently been investigated.

There are several triacylglycerol producing reactions that undergo sn-3 acylation or transacylation reactions, including two classes of DAGAT genes, and a phospholipid:diacylglycerol acyltransferase. One class of DAGAT genes has been isolated and expressed from Arabidopsis based upon their homology to the mammalian DAGAT gene, and more broadly to acyl-CoA:cholesterol acyltransferase (ACAT)-like genes, and by mapping of the gene corresponding to a mutation. A second class of DAGAT genes can be identified based upon homology to a DAGAT first purified from a fungus, *Mortierella ramanniana*. However, a gene has not been identified, much less isolated and expressed, from an organism that exhibits a unique triacylglycerol such as is found in seed oils of the genus *Euonymus*.

Moreover, the availability of a DAGAT with acetyl-CoA: sn-1,2-diacylglycerol acyltransferase activity would allow novel triacylglycerol structures to be produced; such novel triacylglycerol molecules could by synthesized in vitro or in vivo. The presence of an acetyl group rather than a long-chain fatty acid esterified at one or more, but not all, of the positions on the glycerol backbone will reduce the calorific value of the oil while not interfering with its functionality in foods. Also, an oil such as olive oil or high oleic oils, or castor oil, which all contain a large amount of trifunctional triacylglycerols, such as triolein or triricinolein, would easily be converted to bifunctional oils if an acetyl group replaced the fatty acid at the sn-3 position. Such oils would have different industrial applications than their trifunctional counterparts. For example, a bifunctional triacylglycerol would produce linear (thermoplastic) polymers whereas a trifunctional triacylglycerol would produce cross-linked (thermosetting) polymers.

Therefore, it would be desirable to be able to generate vegetable oils with high amounts of acetyl glycerides, and in particular sn-3-acetyl glycerides. One route is by identifying and isolating a plant gene that is capable of synthesizing acetyl glycerides. Such a gene could then be used to transform oil crop plants. Identification of such a gene could also be used to synthesize novel acetyl glycerides that do not exist naturally.

SUMMARY OF THE INVENTION

Thus, in some embodiments, the present invention provides an isolated nucleic acid sequence encoding a diacylglycerol acetyltransferase. In some further embodiments, the diacylglycerol acetyltransferase is from a plant of the genus *Euonymus*. In yet further embodiments, the plant is a *Euonymus alata* plant. In yet further embodiments, the nucleic acid sequence encodes SEQ ID NO:2. And in yet further embodiments, the nucleic acid sequence comprises SEQ ID NO: 1.

In other embodiments, the present invention provides an isolated nucleic acid sequence encoding a polypeptide comprising SEQ ID NO:2. In yet other embodiments, the present invention provides an isolated nucleic acid sequence that hybridizes under conditions of high stringency to a nucleic sequence comprising SEQ ID NO: 1, wherein the sequence encodes a diacylglycerol acetyltransferase.

In other embodiments, the present invention provides an isolated antisense sequence corresponding to any of the nucleic acid sequences described above. In some embodiments, the present invention provides an interfering RNA targeted to a sequence in an mRNA transcribed from any of the nucleic acid sequences described above. In some further embodiments, the present invention provides a nucleic acid sequence encoding any of the interfering RNAs described above.

In other embodiments, the present invention provides any of the nucleic acid sequences described above operably linked to a heterologous promoter. In yet further embodiments, the nucleic acid sequences described above operably linked to a heterologous promoter are in a vector. In other embodiments, the present invention provides a vector comprising any of the nucleic acid sequences described above.

In some embodiments, the present invention provides a purified polypeptide encoded by any of the nucleic acid sequences described above, where the nucleic acid sequences encode a diacylglycerol acetyltransferase. In other embodiments, the present invention provides a purified diacylglycerol acetyltransferase. In some further embodiments, the diacylglycerol acetyltransferase is from a plant of the genus *Euonymus*. In yet further embodiments, the plant is a *Euonymus alata*. In yet further embodiments, the purified diacylglycerol acetyltransferase comprises SEQ ID NO:2. In other embodiments, the present invention provides a purified polypeptide comprising SEQ ID NO:2.

In other embodiments, the present invention provides a host cell transformed with any of the nucleic acid sequences described above; in particular embodiments, the nucleic acid sequence comprises a heterologous gene encoding a plant diacylglycerol acetyltransferase. In some further embodiments, the host cell is a plant cell or a microorganism. In some further embodiments, the host cell is a microorganism selected from the group consisting of bacteria and yeast. In other embodiments, the present invention provides oil from a transgenic microorganism as described above.

In yet other embodiments, the present embodiment provides a plant or plant part transformed with any of the nucleic acid sequences described above, wherein the plant or plant part is selected from the group consisting of a plant, a plant organ, a plant tissue, and a plant cell; in particular embodiments, the nucleic acid sequence comprises a heterologous gene encoding a plant diacylglycerol acetyltransferase. In some embodiments, the present invention provides a plant seed transformed with any of the nucleic acid sequences described above; in particular embodiments, the nucleic acid sequence comprises a heterologous gene encoding a plant diacylglycerol acetyltransferase. In other embodiments, the present invention provides oil from a transgenic plant as described above.

In some embodiments, the present invention provides a method to identify diacylglycerol acetyltransferase coding sequences, comprising: obtaining a non-cDNA library for DAGAT by using RT-PCR with degenerated primers to give a partial length clone; using 3' and 5' RACE to define the 3' and 5' cDNA ends; obtaining a full length cDNA clone via RT-PCR using primers based on the sequence of the 3' and 5' RACE products; and using the full length cDNA clone to confirm the identity of the encoded polypeptide as a diacylglycerol acetyltransferase (AcDAGAT). In some further embodiments, confirmation of the identity of the encoded polypeptide as an AcDAGAT comprises: expressing the encoded polypeptide of the full length cDNA: and characterizing the expressed polypeptide. In yet further embodiments, characterizing the expressed polypeptide is by detecting the presence of the expressed polypeptide by antibody-binding; in some further embodiments, the antibody is specific for AcDAGAT. In yet other further embodiments, characterizing the expressed polypeptide is by detecting reaction products of the expressed polypeptide in an AcDAGAT activity assay. In some other further embodiments, acetyl glycerides (AcTAGs) are present in the tissue from which the non-cDNA library is prepared.

In some embodiments, the present invention provides a method of producing acetyl glycerides comprising one acetyl group and two long-chain acyl groups, comprising: providing a host cell transformed with a heterologous gene encoding a diacylglycerol acetyltransferase (AcDAGAT); and growing the host cell under conditions sufficient to effect production of acetyl glycerides.

In some embodiments, the present invention provides a method of producing acetyl glycerides comprising one acetyl group and two long-chain acyl groups, comprising: incubating an isolated nucleic acid sequence encoding a diacylglycerol acetyltransferase (AcDAGAT) in an in vitro expression system under conditions sufficient to effect production of acetyl glycerides. In other embodiments, the present invention provides a method of producing acetyl glycerides comprising one acetyl group and two long-chain acyl groups, comprising: incubating an diacylglycerol acetyltransferase (AcDAGAT) in an in vitro reaction mixture under conditions sufficient to effect production of acetyl glycerides. In further embodiments, the expression system or the reaction mixture of the in vitro methods described above further comprises a substrate of AcDAGAT. In other further embodiments, the expression system or reaction mixture of the in vitro methods further comprises means for generating at least one substrate of the AcDAGAT. In other further embodiments, the method of producing acetyl glycerides comprising one acetyl group and two long-chain acyl groups as described above further comprises collecting the acetyl glycerides produced.

In other embodiments, the present invention provides a method for producing novel triglycerides (TAGs), comprising: providing a diacylglycerol substrate to a diacylglycerol acetyltransferase (AcDAGAT) under conditions sufficient to produce a triglyceride produced from the provided substrate, wherein at least one of the fatty acyl chains of the diacylglycerol substrate is selected from the group consisting palmitoleic acid, a ricinoleic acid, divernolic acid, and capric acid.

In yet other embodiments, the present invention provides a method for producing novel triglycerides (TAGs), comprising: providing at least one of acetyl-CoA, propionyl-CoA, butyryl-CoA, benzoyl-CoA, or cinnamoyl-CoA substrate to a diacylglycerol acetyltransferase (AcDAGAT) under conditions sufficient to produce a triglyceride comprising the provided acetyl, propionyl, butyryl, benzoyl, or cinnamoyl group.

In yet other embodiments, the present invention provides a novel triglyceride produced by any of the methods described above. In yet other embodiments, the present invention provides a novel triglyceride, wherein the triglyceride is an acetyldipalmitolein, propionyldipalmitolein, butyryldipalmitolein, benzoyldipalmitolein, cinnamoyldipalmitolein, acetyldiricinolein, acetyldivernolin, or acetyldicaprin.

DESCRIPTION OF THE FIGURES

FIG. 5 shows the nucleotide sequence of *Euonymus alata* seed diacylglycerol acetyltransferase (EaDAGAT) cDNA (SEQ ID NO:1).

FIG. 6 shows the deduced amino acid sequence (SEQ ID NO:2) encoded by the nucleotide sequence of the *Euonymus alata* seed diacylglycerol acyltransferase (EaDAGAT) cDNA shown in FIG. 5.

FIG. 7 shows an alignment of the deduced amino acid sequences of the DAGAT genes of *Euonymus alata* (E.a.) (SEQ ID NO:17), *Arabidopsis thaliana* (A.t.) (SEQ ID NO:18), *Nicotiana tabaccum* (N.t.) (SEQ ID NO:19), and *Perilla frutescens* (P.f.) (SEQ ID NO:20). The highlighting indicates identical amino acids for at least two genes in the four gene alignment.

GENERAL DESCRIPTION OF THE INVENTION

Figure 1:
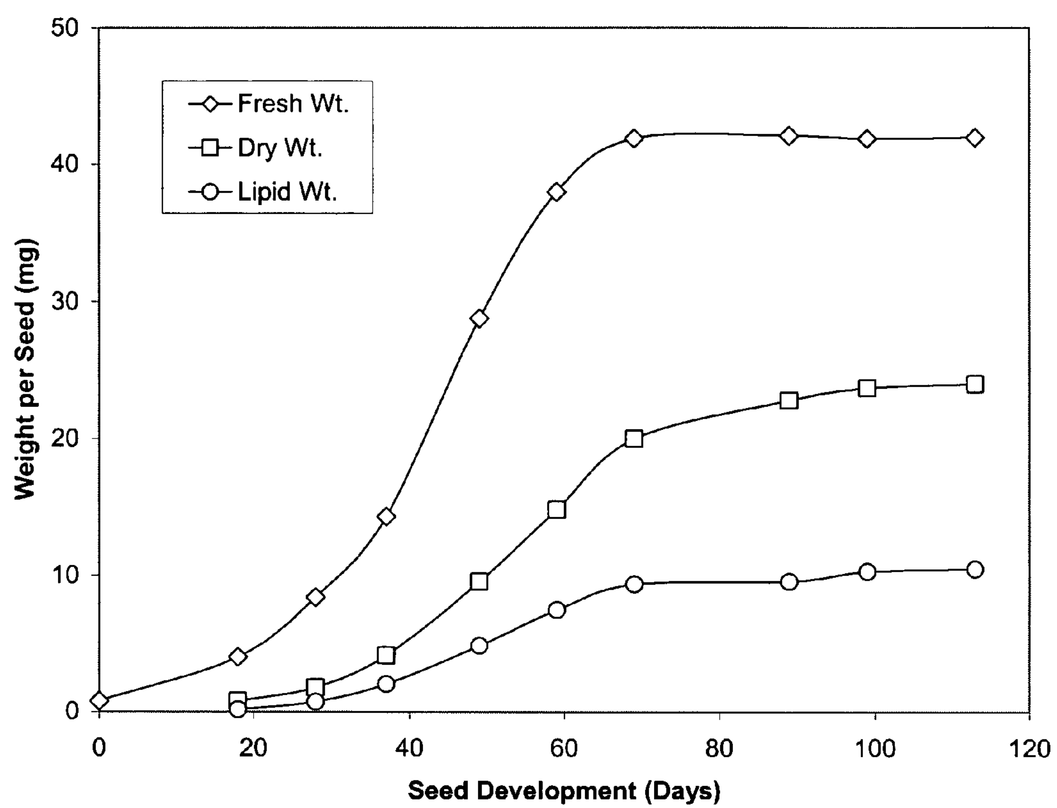
FIG. 1 shows the accumulation of fresh weight, dry weight, and total lipids in developing *Euonymus alata* seeds.

The present invention relates to compositions comprising diacylglycerol acyltransferase (DAGAT) genes and polypeptides, and in particular *Euonymus* and *Euonymus*-like DAGAT genes and polypeptides, where the enzyme exhibits an increased specificity for acetyl-CoA or the CoA esters of groups related to acetate (described further below). These polypeptides are referred to as diacylglycerol acetyltransferase, designated "AcDAGAT," indicating an activity of increased specificity for transfer of acetyl or related groups, and/or "EaDAGAT," indicating an enzyme obtained from *Euonymus alata*. The present invention encompasses compositions comprising both native and recombinant forms of the enzyme, as well as mutant and variant forms, some of which possess altered characteristics relative to the wild-type. The present invention also comprises novel triacylglycerols synthesized by AcDAGAT. The present invention also provides methods for using AcDAGAT genes and polypeptides.

In some embodiments, the present invention provides novel isolated nucleic acid sequences encoding an AcDAGAT. In other embodiments, the invention provides isolated nucleic acid sequences encoding mutants, variants, homologs, chimeras, and fusions of an AcDAGAT. In other embodiments, the present invention provides methods of generating such sequences. In other embodiments, the present invention provides methods of cloning and expressing such sequences, as well as methods of purifying and assaying the expression product of such sequences.

In additional embodiments, the present invention provides purified AcDAGAT polypeptides. In other embodiments, the present invention provides mutants, variants, homologs, chimeras, and fusion proteins of AcDAGAT. In some embodiments, the present invention provides methods of purifying, and assaying the biochemical activity of wild type as well as mutants, variants, homologs, chimeras, and fusions of AcDAGAT, as well as methods of generating antibodies to such proteins.

In other embodiments, the present invention provides compositions comprising novel triacylglycerols synthesized by an AcDAGAT of the present invention. Such syntheses may be accomplished by any of the methods described below.

In some embodiments, the present invention provides methods of using novel isolated nucleic acid sequences encoding an AcDAGAT to produce products of the acetyltransferase activity. In some embodiments, the methods involve adding the sequences to in vitro transcription and translations systems that include the substrates of the AcDAGAT, such that the products of the acetyltransferase may be recovered. In other embodiments, the methods involve transforming organisms with the sequences such that the sequences are expressed and products of the AcDAGAT are produced. In particular embodiments, the products are recovered. In other embodiments, the products remain in situ.

In some embodiments, the present invention provides methods of using recombinant AcDAGAT polypeptides to produce products of the acetyltransferase activity. In some embodiments, the methods involve adding the polypeptides to in vitro systems which include the substrates of the AcDAGAT, such that the products of the AcDAGAT may be recovered.

In other embodiments, the methods involve transforming a plant with a novel isolated nucleic acid sequence encoding an AcDAGAT such that products of the AcDAGAT are produced.

In some embodiments, the present invention provides an organism transformed with heterologous gene encoding an AcDAGAT. In some embodiments, the organism is a microorganism. In other embodiments, the organism is a plant.

In some embodiments, the present invention also provides a cell transformed with a heterologous gene encoding an AcDAGAT. In some embodiments, the cell is a microorganism. In other embodiments, the cell is a plant cell.

In other embodiments, the present invention provides a plant seed transformed with a nucleic acid sequence encoding an AcDAGAT.

In yet other embodiments, the present invention provides an oil from a plant, a plant seed, or a microorganism transformed with a heterologous gene encoding an AcDAGAT.

DEFINITIONS

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae (for example, *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture. The term "plant part" as used herein refers to a plant structure or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term "oil-producing species" refers to plant species that produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids.

The term "*Euonymus*" refers to a plant or plants from the genus *Euonymus*. Non-limiting examples of *Euonymus* include plants from the species *E. alata*. The term also refers to *E. alata* plants from which nucleic acid sequence SEQ ID NO:1 was isolated.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "host cell" refers to any cell capable of replicating and/or transcribing and/or translating a heterologous gene.

The terms "diacylglycerol" and "diglyceride" refer to a molecule comprising a glycerol backbone to which two acyl groups are esterified. Typically, the acyl groups are esterified to the sn-1 and sn-2 positions, although the acyl groups may also be esterified to the sn-1 and sn-3 positions, or to the sn-2 and sn-3 positions; the remaining position is unesterified and contains a hydroxyl group. This term may be represented by the abbreviation DAG.

The terms "triacylglycerol" and "triglyceride" refer to a molecule comprising a glycerol backbone to which three acyl groups are esterified. This term may be represented by the abbreviation TAG.

The term "long chain triacylglycerol" refers to a triacylglycerol in which all three acyl groups are long chain, or in other words each chain is a linear aliphatic chain of 6 carbons or greater in length (an acyl group may be referred to by the letter C followed by the number of carbons in the linear aliphatic chain, as, for example, C6 refers to an acyl group of 6 carbons in length). This term may be represented by the abbreviation LcTAG.

The terms "acetyl glyceride" and "acetyl triacylglycerol" and the like refer to a triglyceride to which at least one acetyl or related group is esterified to the glycerol backbone. A particular acetyl glyceride is denoted by the position(s) to which an acetyl or related group is esterified; thus, "sn-3-acetyl glyceride" or "1,2-diacyl-3-acetin" refers to triacylglycerol with an acetyl group at the sn-3 position. These terms may be represented by the abbreviation AcTAG.

An "acetyl" or "related group", when used in reference to AcTAG, refers to an acyl moiety other than a long-chain acyl group esterified to TAG. The acyl moiety is any linear aliphatic chain of less than 6 carbons in length; it may or may not have side group chains or substituents. The acyl moiety may also be aromatic. Related group members include but are not limited to propionyl and butyryl groups, and aromatic groups such as benzoyl and cinnamoyl.

The term "diacylglycerol acyltransferase" refers to a polypeptide with the capacity to transfer an acyl group to a diacylglycerol substrate. Typically, a diacylglycerol acyltransferase transfers an acyl group to the sn-3 position of the diacylglycerol, though transfer to the sn-1 and sn-2 positions are also possible. The acyl substrate for the transferase is typically esterified to CoA; thus, the acyl substrate is typically acyl-CoA. The enzyme is therefore also referred to as an "diacylglycerol:acyl-CoA acyltransferase," and in some particular embodiments, as an "acyl-CoA:sn-1,2-diacylglycerol acyltransferase," and the like. The term may be referred to by the abbreviation DAGAT.

The term "diacylglycerol acetyltransferase" refers to a diacylglycerol acyltransferase polypeptide with a unique acyl group transfer specificity, such that the polypeptide is able to transfer an acetyl or related group to a diacylglycerol substrate, and such that the diacylglycerol acetyltransferase exhibits increased specificity for an acetyl or related group compared to a diacylglycerol acyltransferase obtained from a plant in which acetyl TAGs are not present, or are present in only trace amounts (in other words, less than about 1% of the total TAGs). The specificity may be determined by either in vivo or in vitro assays. From an in vivo assay, the specificity is the proportion of total TAGs that are AcTAGs, where the AcTAGs are synthesized by the presence of a heterologous diacylglycerol acetyltransferase. From an in vitro assay, the specificity is the activity of transfer of an acetyl or related group to a diacylglycerol, when the substrate is an acetyl-CoA or related group esterified to CoA. The increase in specificity of transferring an acetyl or related group for an AcDAGAT is at least about 1.5 times, or about 2 times, or about 5 times, or about 10 times, or about 20 times, or about 50 times, or about 100 times, or up to about 2000 times, the specificity of a DAGAT obtained from a plant in which acetyl TAGs are not present, or are present in only trace amounts. One standard DAGAT to which an AcDAGAT is compared, in order to determine specificity of transfer of an acetyl or related group, is a DAGAT obtained from *Arabidopsis* (AtDAGAT), as described in Example 4.

The acetyl or related group substrate of the transferase is typically esterified to CoA; thus, typical acetyl substrate include but are not limited to acetyl-CoA, propionyl-CoA, butyryl-CoA, benzoyl-CoA, or cinnamoyl-CoA, as described above. These CoA substrates are typically non-micellar acyl-CoAs, or possess high critical micelle concentrations (CMCs), in that they form micelles at relatively high concentrations when compared to the CMCs of long chain acyl-CoAs.

The diacylglycerol substrate of AcDAGAT is typically a long chain diacylglycerol, although other groups are also contemplated. The acyl (or other) groups are esterified to the sn-1 and sn-2 positions, although the acyl groups may also be esterified to the sn-1 and sn-3 positions, or to the sn-2 and sn-3 positions.

Thus, the enzyme is also referred to as an "diacylglycerol: acetyl-CoA acetyltransferase," or in particular embodiments, as an "acetyl-CoA:sn-1,2-diacylglycerol acetyltransferase" and the like. This term may be referred to by the abbreviation AcDAGAT, indicating an activity of increased specificity for transfer of acetyl or related groups.

The terms "*Euonymus*" and "*Euonymus*-like" when used in reference to a DAGAT refer to a DAGAT obtained from *Euonymus alata* or with a substrate specificity that is similar to a DAGAT obtained from *Euonymus alata*. The term may be referred to by the abbreviation, "EaDAGAT," indicating an enzyme obtained from *Euonymus alata*, or from the genus *Euonymus*, or from the closely related plant family Celestraceae, or an enzyme which has an amino acid sequence with a high degree of similarity to or identity with a DAGAT obtained from *Euonymus alata*. By "high degree of similarity" it is meant that it is more closely related to EaDAGAT than to AtDAGAT by BLAST scores or other amino acid sequence comparison/alignment software programs.

The term "substrate specificity" refers to the range of substrates that an enzyme will act upon to produce a product.

The term "competes for binding" is used in reference to a first polypeptide with enzymatic activity which binds to the same substrate as does a second polypeptide with enzymatic activity, where the second polypeptide is variant of the first polypeptide or a related or dissimilar polypeptide. The efficiency (for example, kinetics or thermodynamics) of binding by the first polypeptide may be the same as or greater than or less than the efficiency substrate binding by the second polypeptide. For example, the equilibrium binding constants ($K_D$) for binding to the substrate may be different for the two polypeptides.

The terms "protein" and "polypeptide" refer to compounds comprising amino acids joined via peptide bonds and are used interchangeably.

As used herein, "amino acid sequence" refers to an amino acid sequence of a protein molecule. "Amino acid sequence" and like terms, such as "polypeptide" or "protein," are not meant to limit the amino acid sequence to the complete, native amino acid sequence associated with the recited protein molecule. Furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "homology" when used in relation to amino acids refers to a degree of similarity or identity. There may be partial homology or complete homology (in other words, identity). "Sequence identity" refers to a measure of relatedness between two or more proteins, and is given as a percentage with reference to the total comparison length. The identity calculation takes into account those amino acid residues that are identical and in the same relative positions in their respective larger sequences. Calculations of identity may be performed by algorithms contained within computer programs.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferable greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (for example, replacement of leucine with isoleucine). More rarely, a variant may have "non-conservative" changes (for example, replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (for example, DNA or RNA) sequence that comprises coding sequences necessary for the production of RNA, or a polypeptide or its precursor (for example, proinsulin). A functional polypeptide can be encoded by a full length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

The term "heterologous gene" refers to a gene encoding a factor that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene;

the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence that is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (in other words, it is the complement of) the single-stranded nucleic acid sequence under conditions of low to high stringency as described above.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% G+C)$, when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q βreplicase, MDV-1 RNA is the specific template for the replicase (Kacian et al. (1972) Proc. Natl. Acad. Sci. USA, 69:3038). Other nucleic acid will not be replicated by this amplification enzyme. Similarly, in the case of T7 RNA polymerase, this amplification enzyme has a stringent specificity for its own promoters (Chamberlin et al. (1970) Nature, 228:227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics, 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) *PCR Technology*, Stockton Press).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "RACE" refers to Rapid Amplification of cDNA Ends.

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (in other words, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (in other words precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (for example, peroxidase conjugated) secondary antibody that is specific for the primary antibody is allowed to bind to the sectioned tissue and specific binding detected (for example, with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, incorporated herein by reference), mannopine synthase, octopine synthase (ocs), superpromoter (see for example, WO 95/14098), and ubi3 (see for example, Garbarino and Belknap (1994) Plant Mol. Biol. 24:119–127) promoters. Such promoters have been used successfully to direct the expression of heterologous nucleic acid sequences in transformed plant tissue.

In contrast, a "regulatable" promoter is one that is capable of directing a level of transcription of an operably linked nuclei acid sequence in the presence of a stimulus (for example, heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. (1989) *Molecular Cloning: A Laboratory Manual,* 2nd ed., Cold Spring Harbor Laboratory Press, New York, pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6–16.7).

The term "selectable marker" refers to a gene which encodes an enzyme having an activity that confers resistance to an antibiotic or drug upon the cell in which the selectable marker is expressed, or which confers expression of a trait which can be detected (for example., luminescence or fluorescence). Selectable markers may be "positive" or "negative." Examples of positive selectable markers include the neomycin phosphotransferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "vector refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (in other words, particle bombardment) and the like.

The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium that causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (for example, nopaline, agropine, octopine etc.) by the infected cell. Thus, *Agrobacterium* strains which cause production of nopaline (for example, strain LBA4301, C58, A208, GV3101) are referred to as "nopaline-type" *Agrobacteria; Agrobacterium* strains which cause production of octopine (for example, strain LBA4404, Ach5, B6) are referred to as "octopine-type" *Agrobacteria*; and *Agrobacterium* strains which cause production of agropine (for example, strain EHA105, EHA101, A281) are referred to as "agropine-type" *Agrobacteria.*

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator (PDS-1000/He, Bio-Rad).

The term “microwounding” when made in reference to plant tissue refers to the introduction of microscopic wounds in that tissue. Microwounding may be achieved by, for example, particle bombardment as described herein.

The term “transgenic” when used in reference to a plant or fruit or seed (in other words, a “transgenic plant” or “transgenic fruit” or a “transgenic seed”) refers to a plant or fruit or seed that contains at least one heterologous gene in one or more of its cells. The term “transgenic plant material” refers broadly to a plant, a plant structure, a plant tissue, a plant seed or a plant cell that contains at least one heterologous gene in one or more of its cells.

The terms “transformants” or “transformed cells” include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term “wild-type” when made in reference to a gene refers to a gene that has the characteristics of a gene isolated from a naturally occurring source. The term “wild-type” when made in reference to a gene product refers to a gene product that has the characteristics of a gene product isolated from a naturally occurring source. A wild-type gene is that which is most frequently observed in a population and is thus arbitrarily designated the “normal” or “wild-type” form of the gene. In contrast, the term “modified” or “mutant” when made in reference to a gene or to a gene product refers, respectively, to a gene or to a gene product which displays modifications in sequence and/or functional properties (in other words, altered characteristics) when compared to the wild-type gene or gene product. It is noted that naturally-occurring mutants can be isolated; these are identified by the fact that they have altered characteristics when compared to the wild-type gene or gene product.

The term “antisense” refers to a deoxyribonucleotide sequence whose sequence of deoxyribonucleotide residues is in reverse 5' to 3' orientation in relation to the sequence of deoxyribonucleotide residues in a sense strand of a DNA duplex. A “sense strand” of a DNA duplex refers to a strand in a DNA duplex that is transcribed by a cell in its natural state into a “sense mRNA.” Thus an “antisense” sequence is a sequence having the same sequence as the non-coding strand in a DNA duplex. The term “antisense RNA” refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. “Ribozyme” refers to a catalytic RNA and includes sequence-specific endoribonucleases. “Antisense inhibition” refers to the production of antisense RNA transcripts capable of preventing the expression of the target protein.

The term “siRNAs” refers to short interfering RNAs. In some embodiments, siRNAs comprise a duplex, or double-stranded region, of about 18–25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the “antisense strand;” the strand homologous to the target RNA molecule is the “sense strand,” and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term “target RNA molecule” refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The term “RNA interference” or “RNAi” refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term “posttranscriptional gene silencing” or “PTGS” refers to silencing of gene expression in plants after transcription, and appears to involve the specific degradation of mRNAs synthesized from gene repeats.

The term “overexpression” refers to the production of a gene product in transgenic organisms that exceeds levels of production in normal or non-transformed organisms. The term “cosuppression” refers to the expression of a foreign gene that has substantial homology to an endogenous gene resulting in the suppression of expression of both the foreign and the endogenous gene. The term “altered levels” refers to the production of gene product(s) in transgenic organisms in amounts or proportions that differ from that of normal or non-transformed organisms.

The term “recombinant” when made in reference to a nucleic acid molecule refers to a nucleic acid molecule that is comprised of segments of nucleic acid joined together by means of molecular biological techniques. The term “recombinant” when made in reference to a protein or a polypeptide refers to a protein molecule that is expressed using a recombinant nucleic acid molecule.

The terms “Southern blot analysis” and “Southern blot” and “Southern” refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31–9.58).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39–7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a plant DAGAT includes, by way of example, such nucleic acid in cells ordinarily expressing a DAGAT, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and anti-sense strands (in other words, the oligonucleotide may be double-stranded).

The term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. The term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DETAILED DESCRIPTION OF THE INVENTION

The present invention provides compositions comprising isolated diacylglycerol acyltransferase (DAGAT) genes and polypeptides, and in particular to compositions comprising isolated *Euonymus* and *Euonymus*-like DAGAT genes and polypeptides, where the enzyme exhibits an increased specificity for acetyl-CoA. These polypeptides are referred to as diacylglycerol acetyltransferase, designated "AcDAGAT," indicating an activity of increased specificity for transfer of acetyl or related groups, and/or "EaDAGAT," indicating an enzyme obtained from *Euonymus alata*. The present invention also provides compositions comprising both native and recombinant forms of the enzyme, as well as mutant and variant forms, some of which possess altered characteristics relative to the wild-type. The present invention also provides compositions comprising novel triacylglycerols, which can be synthesized by an AcDAGAT, such as acetyldipalmitolein, acetyldiolein, acetyldiricinolein, and acetyldivernolin. The present invention also provides methods for using AcDAGAT genes and polypeptides.

The description below provides specific, but not limiting, illustrative examples of embodiments of the present invention. This description includes a discovery of an AcDAGAT from *Euonymus*, AcDAGAT polypeptides of the present invention, AcDAGAT coding sequences of the present invention, methods of identifying AcDAGATs proteins and coding sequences, methods of expressing AcDAGAT coding sequences, methods of producing acetyl glycerides, and methods of manipulating diacylglycerol acetyltransferase activity in plants.

I. Discovery of Diacylglycerol Acetyltransferase Gene and Polypeptide in *Euonymus*

Although the occurrence and structural characterization of the unusual sn-3-acetyl triacylglycerols in seed oils has been known for over thirty years (Kleiman et al. (1967) Lipids 2:473–478), the biosynthesis of these novel glycerides has only recently been investigated. These unusual triacylglycerols are found in varying amounts in a few plant species, but in *Euonymus* species they represent up to 98% of the total triacylglycerols in the seed oil. Thus, *Euonymus* was selected as a potential source from which an acyl-CoA: sn-1,2-diacylglycerol acyltransferase gene could be identified and isolated.

In the *Euonymus* sn-3-acetyl glycerides, the sn-1 and sn-2 positions are esterified with common long-chain fatty acids, predominantly palmitate, oleate and linoleate. Investigations of the biosynthesis of sn-3-acetyl glycerides in *Euonymus* revealed that sn-3-acetyl glycerides are synthesized by a DAGAT activity. These investigations included studies of the tissue distribution of the acetyl glycerides, of in vivo labeling of developing seeds with [$^{14}$C]acetate, and of an assay of acetyltransferase in cell free extracts in *Euonymus alata*, an ornamental shrub common to the Mid-West. The common name for this plant is Burning Bush, from its distinctive red autumn foliage.

Figure 2:
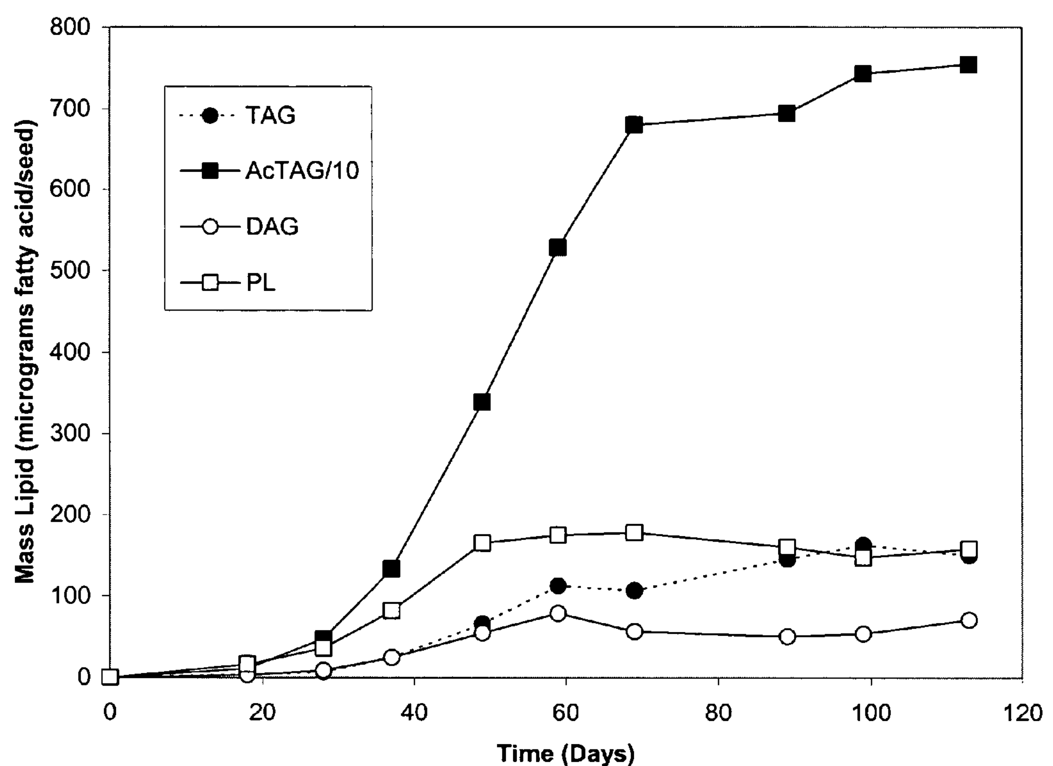
FIG. 2 shows the accumulation of 1,2-diacyl-3-acetins (AcTAG), normal triacylglycerols (TAG), diacylglycerols (DAG) and polar lipids (PL) in developing *Euonymus* seed (embryo and endosperm). To keep the AcTAG on the same scale as the other lipid classes its value has been compressed 10-fold.
Figure 3:
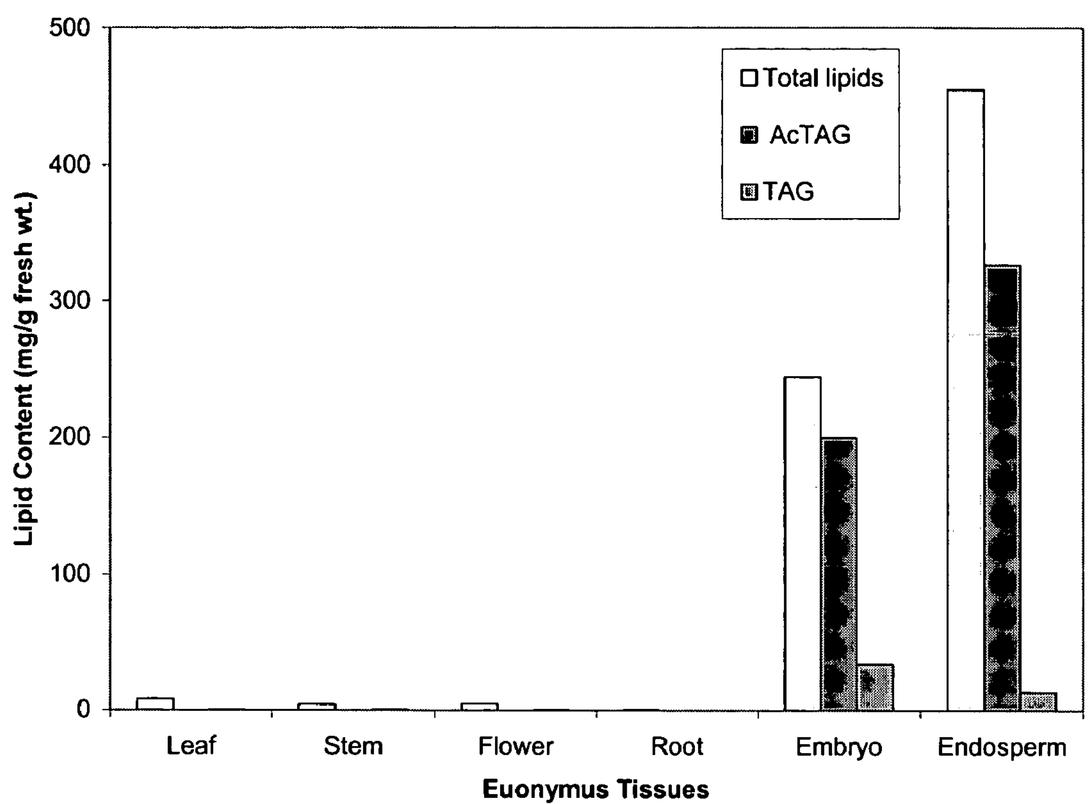
FIG. 3 shows the accumulation of total lipids, 1,2-diacyl-3-acetins (AcTAG) and normal triacylglycerols (TAG) in developing *Euonymus* seed (embryo and endosperm) and other tissues.

Tissue distribution of 1,2-diacyl-3-acetins and long chain triacylglycerols. The accumulation of seed oil was examined over seed development; the results are shown in FIGS. 1 and 2. The results indicated an endogenous rate of accumulation of 1,2-diacyl-3-acetins (AcTAG) of about 0.5 mmoles/hour/gram fresh weight seed at mid-maturation. In addition, various tissues were analyzed for the presence and amounts of total lipids, 1,2-diacyl-3-acetins (AcTAG), and normal triacylglycerols (TAG); the results are shown in FIG. 3. The glycerides were analyzed using high temperature gas chromatography (GC) with odd-chain internal standards. As expected, the largest amounts of lipids were found in embryo and endosperm tissue. TAGs were found in all tissues except root. AcTAG was found to be specific for embryo tissue, and was most predominant in endosperm tissue. Thus, AcTAG was not observed in leaves, stems, roots, or developing floral buds.

Figure 4:
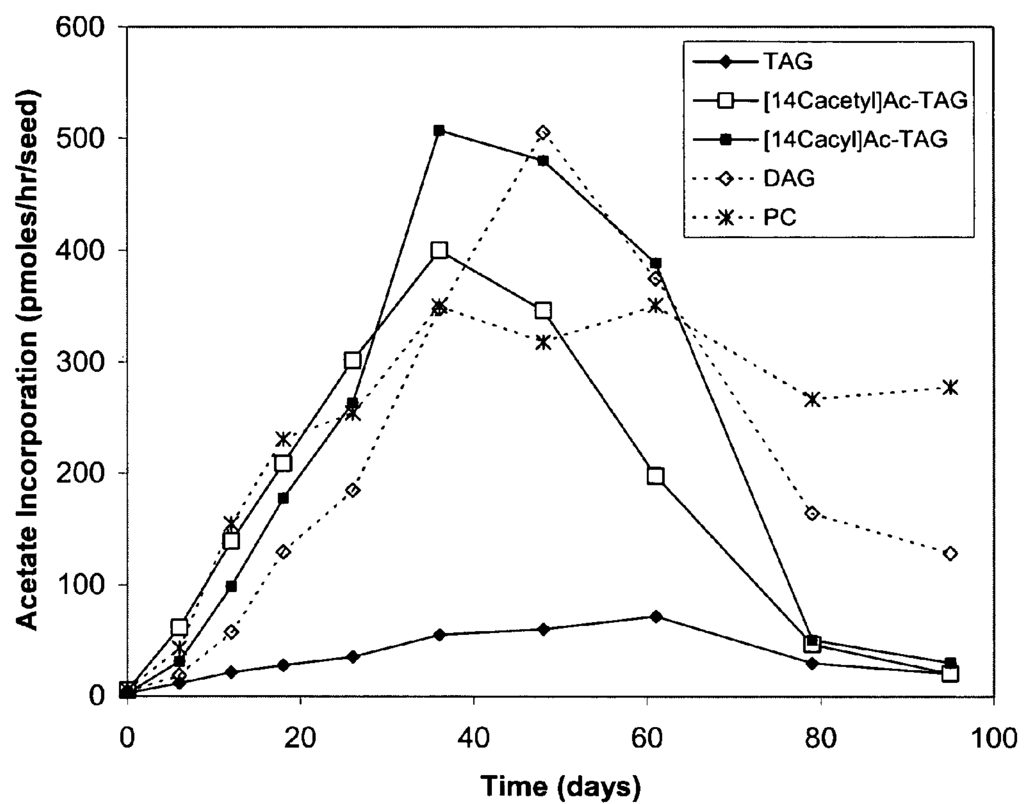
FIG. 4 shows [$^{14}$C] acetate incorporation into the major acyl lipid classes by halved *Euonymus* seeds as a function of seed development. The major lipid classes are long-chain triacylglycerol (TAG), 1,2-diacyl-3-acetin (AcTAG), 1,2-diacylglycerol (DAG) and phosphatidyl-choline (PC). For 1,2-diacyl-3-acetin, the incorporation of label in sn-3 acetyl group and the sn-1 and sn-2 labeled fatty acids is shown separately, as each can be determined independently.

In vivo labeling of developing *Euonymus alata* seeds with [$^{14}$C]acetate. The incorporation of [$^{14}$C]acetate into the major acyl lipid classes, namely long-chain triacylglycerol (TAG), 1,2-diacyl-3-acetin (Ac-TAG), 1,2-diacylglycerol (DAG) and phosphatidyl-choline (PC), was examined in halved seeds as a function of seed development; the results are shown in FIG. 4. The major period of endogenous lipid deposition is from day 20 to day 60, which coincides with the maximum labeling of AcTAG. AcTAG is labeled both in the acetyl group and in the fatty acids, with approximately equal labeling of fatty acids at sn-1 and sn-2 positions. Specific activity per C2 unit is much higher for sn-3 acetyl labeling (1 unit/molecule) when compared to fatty acid labeling (17 or 18 C2 units/molecule).

Time course for *Euonymus alata* seed labeling with [$^{14}$C]acetate. The incorporation of [$^{14}$C]acetate into the major acyl lipid classes by halved seeds was examined as a function of incubation time. Incorporations of acetate into total lipids and into total fatty acids are linear with time. More significantly, incorporation into the sn-3 acetyl group of 1,2-diacyl-3-acetins is also linear. There is no apparent lag phase that would indicate that there is an intermediate acetyl pool which then provides acetyl groups to the sn-3 position of glycerides by a transacylase mechanism. This is consistent with direct utilization of acetyl-CoA for the acylation of diacylglycerol (DAG).

Neither phosphatidylcholine (PC) nor diacylglycerol (DAG) containing a [$^{14}$C]acetyl group was present amongst the reaction products. Moreover, acetate is used preferentially for the sn-3 acetylation of DAG when compared to de novo fatty acid synthesis. This is consistent with a cytosolic acetyl-transferase reaction.

Characterization of acyltransferase activity by in vitro assays. Acyltransferase activity was assayed by incubating [$^{14}$C]acetyl-CoA with cell free extracts from developing *Euonymus alata* seeds and exogenous 1,2-diacylglycerol (DAG). Total lipids were extracted, radioactivity assayed, then the amount of label in the 1,2-diacyl-3-acetin fraction determined by TLC. There was a very high (greater than about 20-fold), largely soluble acetyl-CoA hydrolase activity that competed with the transferase for substrate. Cofactor additions that would generate other activated acetyl donors, namely UDP-glucose to give 1-O-acetyl-glucose or carnitine plus carnitine acetyltransferase to give acetyl carnitine, did not enhance activity.

It was determined that the acetyltransferase can use either endogenous or exogenous 1,2-diacylglycerols as acetyl acceptors. Endogenous DAG are C18C18 or C16C18 species (C18/C16). For an exogenous DAG, both 1,2-diolein (C18/C18) and 1,2-dihexanoin (C6/C6) were used. Dihexanoin was observed to compete with endogenous DAG as the acetyl acceptor. From an acetyl-CoA concentration curve, an estimate Of $V_{max}$ of 120 nmoles/hour/gram fresh weight seed tissue was calculated. This may be compared to the endogenous rate of about 500 nmoles/hour/gram fresh weight seed tissue.

Normal-phase silica TLC was routinely used for product analysis. The [$^{14}$C]acetyl glyceride bands were recovered and further analyzed by reversed-phase TLC. The results indicated that the labeled AcTAG products co-chromatographed with mass standards (endogenous Ac-TAG for C18/C16 and a synthetic 3-acetyl-1,2-dihexanoin standard for C6/C6).

The incorporation of [$^{14}$C]acetyl groups into [$^{14}$C]acetyl-glyceride showed a linear initial rate with no lag phase, which indicates no detectable [$^{14}$C]acetyl biosynthetic intermediate. This is also consistent with direct utilization of acetyl-CoA for the acetylation of DAG.

Strategy for identifying an AcDAT coding sequence. Based upon the evidence obtained from the investigations of the biosynthesis of sn-3-acetyl glycerides in *Euonymus* described above, a strategy for identifying an AcDAGAT coding sequence was developed. This strategy begins with the observation of the presence of sn-3-acetyl glycerides in a plant tissue. The next step is labeling studies of intact tissues and tissue homogenates, to confirm that the ability to synthesize sn-3-acetyl glycerides is in fact present in the tissue and to determine the exact structure of the reaction substrates and particularly the acetyl donor. The next step is obtaining the correct cDNA from total RNA prepared from tissue (which for *Euonymus* is the developing seeds), which synthesizes sn-3-acetyl glycerides, preferably to a relatively high level. For *Euonymus*, the lipid profiles of developing seeds were analyzed, to determine the developmental stage when sn-3-acetyl glycerides accumulated at the highest rate; seeds obtained at this developmental stage are then used to prepare a cDNA library. A cDNA for AcDAGAT is obtained via RT-PCR using degenerated primers for highly conserved sequences identified from DAGAT gene sequences found in the databases, and subsequently using 3' and 5' RACE to define the 3' and 5' cDNA ends (Described in more detail in Example 3). A full length cDNA clone is obtained via RT-PCR using primers based on the sequence of the 3' and 5' RACE products; this clone is used to confirm the identity of the encoded sequence as an AcDAGAT.

Confirmation that the cloned sequence encodes an AcDAGAT is obtained by expression of the clone in either an in vitro or in vivo system, such that either sn-3-acetyl glycerides are produced only upon expression of the clone, or increased amounts of sn-3-acetyl glycerides are produced only upon expression of the clone. The 3-acetyl glycerides may be produced in cells of an organism, or in an enzyme assay conducted with extracts obtained from an organism. Preferably, the system is in vivo, and the clone transfected into and expressed in a host organism. More preferably, the system in one in which sn-3-acetyl glycerides are not normally produced; a non-limiting example is a system in which the host organism is a yeast strain. Even more preferably, the system possesses or is able to synthesize a suitable substrate, such as dioleoylglycerol (di-18:1-DAG), and is able to tolerate the presence of novel acyl groups in triglycerides; a non-limiting example is a system in the host organism is cultured tobacco cells.

Identification of AcDAGAT coding sequence. This strategy was utilized for developing *Euonymus alata* seeds, as described above and in the Examples, and resulted in the identification and isolation of a full length cDNA coding sequence for a DAGAT, as shown in FIG. 5; the deduced amino acid sequence is shown in FIG. 6. The *Euonymus* AcDAGAT deduced amino acid sequence shares high similarity to DAGATs from other plant sources, as shown in FIG. 7. The deduced amino acid sequence is highly similar to all DAGAT proteins described so far for plants (50.7% identity; 91% similarity). The region of the *Euonymus* AcDAGAT protein that is most different from the other DAGAT proteins is the N-terminal end (amino acids 1–93). Other regions with differences include amino acids 158–200 and 243–268. Ten predicted hydrophobic regions are described for plant DAGATs by Kyte-Doolittle hydropathy plots, as described by Hobbs et al. (1999) FEBS Lett. 452: 145–149, Bouvier-Nave et al. (2000) Eur. J. Biochem. 267: 85–96, Routaboul et al. (1999) Plant physiol. Biochem. 37: 831–840, and Zou et al. (1999) Plant J. 19: 645–653. These regions are present in the EaDAGAT. Seven transmembrane spanning domains have been identified in another member of the DAGAT gene family, namely the human acyl-CoA:cholesterol acyltransferase-1 protein (Lin et al. (1999) J. Biol. Chem. 274: 23276–23285) using an epitope tagging approach. It is possible that a pair of transmembrane domains were missed by this approach. Given the similarity with DAGATs, it is likely that DAGATs have seven or nine actual transmembrane domains. Putative acyl-binding and active sites are described by Jako et al. (2001), Plant Phys 126, 861–874, and by others mentioned above. Putative acyl-binding and putative active sites are shown by underlining in FIG. 7.

Confirmation of the identity of the *Euonymus alata* AcDAGAT (EaDAGAT), and the ability of EaDAGAT to synthesize sn-3-acetyl glycerides (AcTAGs), was obtained by expression of EADAGAT in yeast cells, and observing TAGs synthesized both in vivo in intact yeast cells, and in vitro with transgenic yeast membrane fractions. Expression of *Euonymus* DAGAT (EaDAGAT) in yeast cells resulted in the increased synthesis of long chain triacylglycerols (LcTAG) of about 5 fold (as described in Example 4) when compared to the control (yeast transformed with an empty vector). Moreover, expression of EaDAGAT in yeast cells also resulted in the synthesis of sn-3-acetyl glycerides (AcTAG) to about 0.26% of the amount of LcTAG synthesized. Three molecular species of AcTAG were identified by GC analysis of the hydrogenated AcTAG enriched fraction isolated by TLC; these three species are C16C16, C16C18, and C18C18 (where the molecular species is identified by the length of the two fatty acyl residues at the sn1 and sn-2 positions). The C16C18 AcTAG species was identified by mass spectroscopy as acetyl-palmitoylsteroylglycerol, which corresponds to acetyl-palmitoleoyloleoylglycerol before hydrogenation.

Expression of *Arabidopsis* DAGAT (AtDAGAT) in yeast cells also resulted in increased synthesis of LcTAG (about 20 fold over control levels), as well as in synthesis of AcTAG (about 0.09% of the amount of LcTAG). Thus, EaDAGAT exhibits an increased propensity to synthesize AcTAG when compared to AtDAGAT in vivo in yeast cells (about 3 fold, when determined as the proportion of total TAGs synthesized). This enhanced propensity to synthesize AcTAG in vivo demonstrates an increased substrate specificity of the EaDAGAT for acetyl-CoA in vivo.

From in vitro assays, when assayed in the presence of an acyl donor, such as oleoyl-CoA, AtDAGAT and EaDAGAT appeared about equally active. However, when assayed in the presence of acetyl-CoA, the AtDAGAT was much less active than the EaDAGAT and resulted in the synthesis of only trace amounts of AcTAG, whereas the EaDAGAT resulted in the synthesis of large amounts of AcTAG. Thus, the EaDAGAT exhibited at least about a 20 fold or greater acetyltransferase activity than did the AtDAGAT. From these results, the EaDAGAT demonstrates a much greater capacity to synthesize AcTAG when provided with an acetyl donor. In summary, these data clearly confirm that the identified *Euonymus* gene encodes a protein which functions as a diacylglycerol acyltransferase (DAGAT) with enhanced ability to synthesize sn-3-acetyl glycerides.

Sequence similarity alone is not sufficient to demonstrate protein function and identity, as demonstrated by the similarities of the different DAGAT amino acid sequences, and their different activities in vivo and in vitro. Confirmation of the identity and activity of EaDAGAT is obtained by expression of the isolated coding sequence and determination of the activity of the encoded protein. However, the EaDAGAT amino acid sequence can be used to discover other AcDAGATs, as is described further below.

II. Diacylglycerol Acetyltransferase Polypeptides

The present invention provides compositions comprising purified diacylglycerol acetyltransferase (AcDAGAT) polypeptides as well as compositions comprising variants of AcDAGAT, including homologs, mutants, fragments, and fusion proteins thereof (as described further below).

In some embodiments of the present invention, the polypeptide is a purified product, obtained from expression of a native gene in a cell, while in other embodiments it may be a product of chemical synthetic procedures, and in still other embodiments it may be produced by recombinant techniques using a prokaryotic or eukaryotic host (for example, by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

A. Reaction Catalyzed

An AcDAGAT is a diacylglycerol acyltransferase polypeptide with a unique acyl group transfer specificity, such that the polypeptide is able to transfer an acetyl or related group to a diacylglycerol substrate, and such that the diacylglycerol acetyltransferase exhibits increased specificity for an acetyl or related group compared to a diacylglycerol acyltransferase obtained from a plant in which acetyl TAGs are not present, or are present in only trace amounts (in other words, less than about 1% of the total TAGs).

Thus, an AcDAGAT polypeptide catalyzes the transfer of an acetyl or related group to diacylglycerol (DAG), as exemplified by the following reaction:

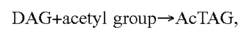

DAG+acetyl group→AcTAG, where the acetyl group is acetyl or a related group, and where the acetyl is transferred to diacylglycerol (DAG) to form acetyl triglycerol (AcTAG). Typically, the acetyl or related group is transferred to the sn-3 position of DAG, although other positions are also contemplated, such as the sn-1 and sn-2 positions of DAG. The enzyme in situ most likely acts on an acetyl group of acetyl-CoA, and most likely transfers the acetyl group to the sn-3 position of DAG. However, the enzyme may utilize different substrates under different conditions to differing degrees of activity, and may produce other products as well. Thus, other substrates may include DAG where the sn-1 or the sn-2 position is available to accept the acetyl group. Other groups transferred include groups related to acetyl, such as propionyl, butyryl, benzoyl, and cinnamoyl; typically, these groups are esterified to Co-A, such that the substrate of the transferase are propionyl-CoA, butyryl-CoA, benzoyl-CoA, or cinnamoyl-CoA.

The specificity of AcDAGAT may be determined by either in vivo or in vitro assays. From an in vivo assay, the specificity is the proportion of total TAGs that are AcTAGs, where the AcTAGs are synthesized by the presence of a heterologous diacylglycerol acetyltransferase. From an in vitro assay, the specificity is the activity of transfer of an acetyl or related group to a diacylglycerol, when the substrate is an acetyl-CoA or related group esterified to CoA. The increase in specificity of transferring an acetyl or related group for an AcDAGAT is at least about 1.5 times, or about 2 times, or about 5 times, or about 10 times, or about 20 times, or about 50 times, or about 100 times, or up to about 2000 times, the specificity of a DAGAT obtained from a plant in which acetyl TAGs are not present, or are present in only trace amounts. One standard DAGAT to which an AcDAGAT is compared, in order to determine specificity of transfer of an acetyl or related group, is a DAGAT obtained from *Arabidopsis* (AtDAGAT), as described in Example 4.

B. *Euonymus* Diacylglycerol Acetyltransferase Polypeptide

In some embodiments, the polypeptide comprises a *Euonymus* DAGAT; in other embodiments, the polypeptide comprises a *Euonymus alata* DAGAT. In one embodiment, the polypeptide is encoded by the sequence shown in FIG. 5 (SEQ ID NO:1); in other embodiments, the polypeptide comprises the amino acid sequence shown in FIG. 6 (SEQ ID NO:2).

As described above under the reaction catalyzed by an AcDAGAT, a particular feature of an AcDAGAT from *Euonymus* is its ability to use acetyl-CoA (or a related group-CoA) instead of long-chain acyl-CoAs. These latter substrates presumably bind to acyl-CoA binding proteins and to membranes, and form micelles by themselves, whereas acetyl-CoA is truly water soluble. Thus the ability of an AcDAGAT to utilize a water-soluble acyl-CoA (or related group-CoA) substrate is an important feature.

C. Variant Diacylglycerol Acetyltransferase Polypeptides

In other embodiments, the present invention provides isolated variants of the disclosed AcDAGAT polypeptides; these variants include mutants, fragments, fusion proteins or functional equivalents of AcDAGAT. Exemplary variants are described further below.

D. Assay of Diacylglycerol Acetyltransferase Polypeptides

The activity of diacylglycerol acetyltransferase (AcDAGAT) may be assayed in a number of ways. These include, but are not limited to, in vivo assays and in vitro assays, as described further below.

In some embodiments, enzyme activity is determined in vivo by expressing a nucleic acid sequence encoding the acetyltransferase in a transgenic organism and then analyzing the content and composition of the TAG fraction present in the transgenic organism. Thus, the activity is measured as the presence of or increase in the amount of endogenous TAG and acetylated TAG (AcTAG) in a transgenic organism which comprises an exogenous nucleic acid sequence having a coding sequence of the present invention (for example, encoding an AcDAGAT, as, for example, SEQ ID NO:2, or comprising an AcDAGAT coding sequence, as, for example, SEQ ID NO: 1); such transgenic organisms are obtained as described below. The amount of TAG and AcTAG in a transgenic organism is compared to that present in a non-transgenic organism. The TAGs are typically analyzed from lipids extracted from samples of a transgenic organism; the samples are homogenized in methanol/chloroform (2:1, v/v) and the lipids extracted as described by Bligh and Dyer (1959) Can. J. Biochem. Physiol. 37: 911–917, or in hexane: isopropanol as described by Hara and Radin (1978) Anal. Biochem. 90: 420–426.

In other embodiments, enzyme activity is determined in vivo by adding exogenous substrates to tissue samples obtained from an organism that may or may not be transgenic (transgenic organisms are described below). For example, in plants, tissue samples include but are not limited to leaf samples (such as discs), stem and root samples, and developing and mature seed embryonic or endosperm tissue. Typically, tissue samples are incubated with [$^{14}$C]acetate substrate, which can be taken up and incorporated into tissue lipids. Incubations generally proceed at room temperature in a buffered solution, such as 0.1M potassium MES at pH 5.5–6.5, for a suitable period of time. The samples are then washed in buffer, and the tissue samples homogenized in methanol/chloroform (2:1, v/v) and the lipids extracted as described by Bligh and Dyer (1959), or in hexane:isopropanol as described by Hara and Radin (1978).

In yet other embodiments, enzyme activity is determined in vitro in a cell-free homogenate or subcellular fraction obtained from an organism which may or may not be transgenic (transgenic organisms are described below), where the tissue is disrupted and filtered or centrifuged to result in cell-free fractions. For example, in plants, subcellular fractions may be obtained from any of the types of tissues described above, and include whole cell and microsomal membranes, plastids and plastid membrane fractions, or other isolated and purified organelles and membranes such as mitochondria and peroxisomes and plasmalemma. The preparation of such fractions is well-known in the art. The subcellular fraction is then incubated with an acetyl- or related group-CoA substrate, such as $^{14}$C-acetyl-CoA, which can be taken up and incorporated into tissue lipids. Additional co-factors for lipid synthesis, as required, may be present during the incubation; such co-factors include but are not limited to DAG. Other reagents which may enhance lipid synthesis may also be added; such reagents include phospholipid liposomes (for example, containing DAG) and lipid transfer proteins. The samples are incubated and the lipids extracted as described above.

In yet other embodiments, enzyme activity is determined from an in-vitro nucleic acid expression system, to which a nucleic acid sequence having a coding sequence of the present invention (for example, encoding an AcDAGAT, as, for example, SEQ ID NO:2, or comprising an AcDAGAT coding sequence, as, for example, SEQ ID NO: 1) is added and the encoded enzyme expressed, and the activity of the expressed enzyme determined. Such expression systems are well-known in the art, and include, for example reticulocyte lysate or wheat germ. The enzyme may be stabilized by the presence of TAGs and/or other glycerolipids, by phosphoglycerolipids that produce membrane structures, or by mixtures of lipids and detergents that produce micellar structures; these structures may be included in the mixture and may include the substrate upon which the enzyme might act, and might include the product produced by the enzyme. It is preferable that such micellar structures are obtained from sources such as from plant tissues where the plant does not contain endogenous diacylglycerol acetyltransferase activity, but which does possess DAG, or other lipids which can be used to produce DAG (such as a glycerolipid), or which can incorporate DAG. Direct and quantitative measurements require the incorporation of labeled lipids into the micellar or membrane structures and the assurance that the utilization of a DAG substrate is not limiting. The activity of newly-expressed enzyme is then analyzed as described above for subcellular fractions.

The extracted lipid products of AcDAGAT are analyzed by methods well-known in the art. For example, the extracted TAG products can be analyzed by normal-phase silica TLC, reversed-phase or silver nitrate TLC (used, for example, for analysis of products first separated by normal-phase silica TLC), high temperature GC (in some cases with odd-chain internal standards), by GC/MS, and by HPLC.

E. Purification of Diacylglycerol Acetyltransferase Polypeptides

In some embodiments of the present invention, a diacylglycerol acetyltransferase (AcDAGAT) polypeptide purified from organisms is provided; such organisms include transgenic organisms, comprising a heterologous AcDAGAT gene, as well as organisms in which AcDAGAT occurs naturally. In other embodiments, an AcDAGAT polypeptide is purified from an in vitro nucleic acid expression system, which comprises a nucleic acid sequence having a coding sequence of the present invention (for example, encoding an AcDAGAT, as, for example, SEQ ID NO:2, or comprising an AcDAGAT coding sequence, as, for example, SEQ ID NO: 1) and from which the expressed AcDAGAT can be purified. The present invention provides a purified AcDAGAT polypeptide as well as variants, including homologs, mutants, fragments, and fusion proteins thereof (as described further below).

The present invention also provides methods for recovering and purifying plant AcDAGAT from an organism or from an in vitro nucleic acid expression system; exemplary organisms include single and multi-cellular organisms. When isolated from an organism, the cells are typically first disrupted and then fractionated before subsequent enzyme purification; disruption and fractionation methods are well-known.

Purification methods are also well-known, and include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, and ioselectric focusing. It is contemplated that AcDAGAT purified in an active or inactive form will require the presence of detergents to maintain its solubility in aqueous media during fractionation. It is further contemplated that assay of the enzyme activity will require removal of the detergent and reconstitution in liposomes to recover full activity. Such methods are well known, for example see Hjelmeland and Chrambach, Furth et al., and van Renswoude and Kempf (1984) Methods in Enzymology 104, p305, 318 and 329 respectively.

The present invention further provides nucleic acid sequences having a coding sequence of the present invention (for example, SEQ ID NO: 1) fused in frame to a marker sequence that allows for expression alone or both expression and purification of the polypeptide of the present invention. A non-limiting example of a marker sequence is a hexahistidine tag that may be supplied by a vector, for example, a pQE-30 vector which adds a hexahistidine tag to the N terminal of an AcDAGAT and which results in expression of the polypeptide in the case of a bacterial host, and in other embodiments by vector PT-23B, which adds a hexahistidine tag to the C terminal of an AcDAGAT and which results in improved ease of purification of the polypeptide fused to the marker in the case of a bacterial host, or, for example, the marker sequence may be a hemagglutinin (HA) tag when a mammalian host is used. The HA tag corresponds to an epitope derived from the influenza hemagglutinin protein (Wilson et al. (1984) Cell 37:767).

F. Chemical Synthesis of Diacylglycerol Acetyltransferase Polypeptides

In some embodiments of the present invention, an AcDAGAT protein is produced using chemical methods to synthesize either an entire AcDAGAT amino acid sequence or a portion thereof. For example, peptides are synthesized by solid phase techniques, cleaved from the resin, and purified by preparative high performance liquid chromatography (See for example, Creighton (1983) *Proteins Structures And Molecular Principles*, W H Freeman and Co, New York N.Y.). In other embodiments of the present invention, the composition of the synthetic peptides is confirmed by amino acid analysis or sequencing (See for example, Creighton, supra).

Direct peptide synthesis can be performed using various solid-phase techniques (Roberge et al. (1995) *Science,* 269: 202–204) and automated synthesis may be achieved, for example, using ABI 431A Peptide Synthesizer (Perkin Elmer) in accordance with the instructions provided by the manufacturer. Additionally, an amino acid sequence of an AcDAGAT, or any part thereof, may be altered during direct synthesis and/or combined using chemical methods with other sequences to produce a variant polypeptide.

G. Generation of Diacylglycerol Acetyltransferase Antibodies

In some embodiments of the present invention, antibodies are generated to allow for the detection and characterization of an AcDAGAT protein. The antibodies may be prepared using various immunogens. In one embodiment, the immunogen is a *Euonymus* AcDAGAT peptide (for example, an amino acid sequence as depicted in SEQ ID NO:2, or fragments thereof) to generate antibodies that recognize *Euonymus* AcDAGAT. Such antibodies include, but are not limited to polyclonal, monoclonal, chimeric, single chain, Fab fragments, and Fab expression libraries.

Various procedures known in the art may be used for the production of polyclonal antibodies directed against an AcDAGAT. For the production of antibody, various host animals can be immunized by injection with the peptide corresponding to an AcDAGAT epitope including but not limited to rabbits, mice, rats, sheep, goats, etc. In a preferred embodiment, the peptide is conjugated to an immunogenic carrier (for example, diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (for example, aluminum hydroxide), surface active substances (for example, lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward an AcDAGAT, it is contemplated that any technique that provides for the production of antibody molecules by continuous cell lines in culture finds use with the present invention (See for example, Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein (1975) Nature, 256: 495–497), as well as the trioma technique, the human B-cell hybridoma technique (See for example, Kozbor et al. (1983) Immunol. Tod., 4:72), and the EBV-hybridoma technique to produce human monoclonal antibodies (Cole et al. (1985) in *Monoclonal Antibodies and Cancer Therapy*, Alan R. Liss, Inc., pp. 77–96).

In addition, it is contemplated that techniques described for the production of single chain antibodies (U.S. Pat. No. 4,946,778) find use in producing an AcDAGAT-specific single chain antibodies. An additional embodiment of the invention utilizes the techniques described for the construction of Fab expression libraries (Huse et al. (1989) Science, 246:1275–1281) to allow rapid and easy identification of monoclonal Fab fragments with the desired specificity for an AcDAGAT.

It is contemplated that any technique suitable for producing antibody fragments finds use in generating antibody fragments that contain the idiotype (antigen binding region) of the antibody molecule. For example, such fragments include but are not limited to: $F(ab')_2$ fragment that can be produced by pepsin digestion of the antibody molecule; Fab' fragments that can be generated by reducing the disulfide bridges of the $F(ab')_2$ fragment, and Fab fragments that can be generated by treating the antibody molecule with papain and a reducing agent.

In the production of antibodies, it is contemplated that screening for the desired antibody is accomplished by techniques known in the art (for example, radioimmunoassay, ELISA (enzyme-linked immunosorbant assay), "sandwich" immunoassays, immunoradiometric assays, gel diffusion precipitin reactions, immunodiffusion assays, in situ immunoassays (for example, using colloidal gold, enzyme or radioisotope labels, for example), Western blots, precipitation reactions, agglutination assays (for example, gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In some embodiments of the present invention, the foregoing antibodies are used in methods known in the art relating to the expression of an AcDAGAT (for example, for Western blotting), measuring levels thereof in appropriate biological samples, etc. The antibodies can be used to detect AcDAGAT in a biological sample from a plant. The biological sample can be an extract of a tissue, or a sample fixed for microscopic examination.

The biological samples are then tested directly for the presence of AcDAGAT using an appropriate strategy (for example, ELISA or radioimmunoassay) and format (for example, microwells, dipstick (for example, as described in International Patent Publication WO 93/03367), etc. Alternatively, proteins in the sample can be size separated (for example, by polyacrylamide gel electrophoresis (PAGE), in the presence or not of sodium dodecyl sulfate (SDS), and the presence of AcDAGAT detected by immunoblotting (Western blotting). Immunoblotting techniques are generally more effective with antibodies generated against a peptide corresponding to an epitope of a protein, and hence, are particularly suited to the present invention.

III. Diacylglycerol Acetyltransferase Coding Sequences

The present invention provides compositions comprising purified nucleic acid sequences encoding any of the diacylglycerol acetyltransferases described above or below. Coding sequences include but are not limited to genes, cDNA, and RNA.

Thus, the present invention provides compositions comprising purified nucleic acid sequences encoding an AcDAGAT, as well as nucleic acid sequences encoding variants of AcDAGAT, including homologs, mutants, or fragments, or fusion proteins thereof, as described above and below. In yet other embodiments, the nucleic acid sequences encode a portion of an AcDAGAT that retains some functional characteristic of a DAGAT. Examples of functional characteristics include the ability to act as an immunogen to produce an antibody that recognizes a DAGAT.

Coding sequences for AcDAGAT include sequences isolated from an organism, which either comprises the coding sequence naturally or is transgenic and comprises a heterologous AcDAGAT coding sequence, sequences which are chemically synthesized, as well as sequences which represent a combination of isolated and synthesized (as, for example, where isolated sequences are mutagenized, or where a sequence comprises parts of sequences isolated from different sources and/or synthesized from different sources).

Thus, in some embodiments of the invention, the coding sequence of a diacylglycerol acetyltransferase (AcDAGAT) is synthesized, whole or in part, using chemical methods well known in the art (See for example, Caruthers et al. (1980) Nucl. Acids Res. Symp. Ser. 7:215–233; Crea and Horn (1980) Nucl. Acids Res. 9:2331; Matteucci and Caruthers (1980) Tetrahedron Lett. 21:719; and Chow and Kempe (1981) Nucl. Acids Res. 9:2807–2817.

A. *Euonymus* Diacylglycerol Acetyltransferase Coding Sequence

In some embodiments, the sequences encode a *Euonymus* diacylglycerol acetyltransferase (AcDAGAT); in other embodiments, the sequences encode a *Euonymus alata* AcDAGAT. In some embodiments, the sequences comprise the sequence shown in FIG. 5 (SEQ ID NO:1); in other embodiments, the sequences encode the amino acid sequence shown in FIG. 6 (SEQ ID NO:2).

B. Variant Diacylglycerol Acetyltransferase Coding Sequences

In other embodiments, the sequences encode a variant of the disclosed diacylglycerol acetyltransferase (AcDAGAT) polypeptides; these variants include mutants, fragments, fusion proteins or functional equivalents of AcDAGAT. Exemplary sequences encoding variants are described further below.

C. Additional Diacylglycerol Acetyltransferase Coding Sequences and Genes

The present invention provides isolated nucleic acid sequences encoding AcDAGAT in addition to those described above. For example, some embodiments of the present invention provide isolated polynucleotide sequences that are capable of hybridizing to SEQ ID NO: 1 under conditions of low to high stringency as long as the polynucleotide sequence capable of hybridizing encodes a protein that retains a desired biological activity of AcDAGAT as described above. In preferred embodiments, hybridization conditions are based on the melting temperature ($T_m$) of the nucleic acid binding complex and confer a defined "stringency" as explained above (See for example, Wahl et al. (1987) Meth. Enzymol., 152:399–407, incorporated herein by reference).

In other embodiments, an isolated nucleic acid sequence encoding an AcDAGAT that is homologous to the *Euonymus* DAGAT is provided; in some embodiments, the sequence is obtained from a plant from families Celastraceae, Lardizabalaceae, Rosaceae and Ranunculaceae.

In other embodiments of the present invention, alleles of an AcDAGAT are provided. In preferred embodiments, alleles result from a mutation, (in other words, a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

These additional AcDAGAT genes are discovered by the methods such as are described below.

IV. Methods of Identifying Diacylglycerol Acetyltransferase Coding Sequences and Genes Other embodiments of the present invention provide methods to isolate nucleic acid sequences encoding AcDAGAT. In some embodiments, the methods include the step of providing plant tissue in which AcTAGs are present; this step is based upon the hypothesis that the presence of AcTAGs in plant tissue, preferably seed tissue, is indicative of the presence of DAGAT with diacylglycerol acetyltransferase activity, or an AcDAGAT. AcTAG is present in a tissue if it is present at greater than about 1% of the total TAGs in that tissue; in preferred embodiments, AcTAGs are present at greater than about 5% of the total TAGs in that tissue, or present at greater than about 10% of the total TAGs in that tissue.

In some embodiments, method involve obtaining a cDNA for DAGAT by using RT-PCR with degenerated primers (exemplary primers are listed in the Examples; alternatively, methods for determining degenerated primers are also provided in the Examples) to give a partial length clone, and subsequently using 3' and 5' RACE to define the 3' and 5' cDNA ends. A full length cDNA clone is then obtained via RT-PCR using primers based on the sequence of the 3' and 5' RACE products; this clone is then used to confirm the identity of the encoded polypeptide as an AcDAGAT. Confirmation of the identity of the encoded polypeptide includes expressing the polypeptide of the sequence encoding a putative AcDAGAT (for example the full length cDNA clone), and characterizing the polypeptide of the putative AcDAGAT coding sequence. Characterization includes but is not limited to detecting the presence of the expressed polypeptide by antibody-binding (where, for example, the antibody is specific for AcDAGAT, such as by binding to *Euonymus* AcDAGAT) or by detecting the reaction products of the expressed polypeptide as in any of the AcDAGAT assays described above. In further embodiments, AcTAGs are present in the tissue from which the cDNA is prepared. Employing this RT-PCR method resulted in the discovery of a *Euonymus* AcDAGAT, as described above and in illustrative Examples. The isolated novel coding sequence was demonstrated to encode a diacylglycerol acetyltransferase, as described in the illustrative Examples. Thus, the nucleotide sequence encoding a *Euonymus* AcDAGAT, and the deduced amino acid sequence of the *Euonymus*, are shown in FIGS. 5 and 6 (SEQ ID NOs: 1 and 2, respectively).

In some other embodiments, methods involve the preparation of a cDNA library from tissue; in further embodiments, AcTAGs are present in the tissue from which the cDNA library is prepared. In some preferred embodiments, AcTAGs are present in relatively high levels, at greater than about 25% of the total TAGs in the tissue, or at greater than about 50% of the total TAGs in the tissue. The cDNA library may be screened by hybridization with a DAGAT probe, or with an AcDAGAT probe (obtained, for example, from SEQ ID NO:1). cDNA clones are identified which appear to encode a DAGAT or an AcDAGAT; in other embodiments, cDNA clones are identified which appear to code for a portion of a DAGAT or AcDAGAT, and which can be assembled into or utilized to create a complete coding sequence. Further embodiments include confirmation of a coding sequence as an AcDAGAT, as described above.

In yet other embodiments, methods involve first an examination of a plant expressed sequence tag (EST) database, in order to discover novel potential DAGAT encoding sequences. Preferably, the plant source of the EST database comprises tissue in which AcTAGs are present, such as its seed tissue. In some embodiments, examination of a plant EST database involves blasting the database with the amino acid sequence of the *Euonymus* AcDAGAT (for example, SEQ ID NO:2), in order to discover ESTs encoding amino acid sequences with homology to the *Euonymus* AcDAGAT protein. In some further embodiments, the methods involve next assembling a clone encoding a complete putative AcDAGAT, and characterizing the expression products of such sequences so discovered as described above. In other further embodiments, these methods next involve sequencing likely candidate sequences, and characterizing the expression products of such sequences so discovered as described above. In some embodiments, AcDAGAT coding sequences, discovered by the methods of the present invention, can also be used to identify and isolate other plant genes. To isolate a gene, a $^{32}$P-radiolabeled AcDAGAT coding sequence (or cDNA) is used to screen, by DNA-DNA hybridization, a genomic library constructed from a plant genomic DNA. In further embodiments, AcTAGs are present in the tissue from which the cDNA is prepared. Single isolated clones that test positive for hybridization are proposed to contain part or all of an AcDAGAT gene, and are sequenced. The sequence of the positive cloned plant genomic DNA is used to confirm the identity of the gene as an AcDAGAT. If a particular clone encodes only part of the gene, additional clones that test positive for hybridization to the AcDAGAT coding sequence (or cDNA) are isolated and sequenced. Comparison of the full-length sequence of a putative AcDAGAT gene to a cDNA is used to determine the location of introns, if they are present.

In other embodiments of the present invention, upstream sequences such as promoters and regulatory elements of a gene encoding an AcDAGAT are detected by extending the gene by utilizing a nucleotide sequence encoding AcDAGAT (for example, SEQ ID NO:1) in various methods known in the art. In some embodiments, it is contemplated that polymerase chain reaction (PCR) finds use in the present invention. This is a direct method that uses universal primers to retrieve unknown sequence adjacent to a known locus (Gobinda et al. (1993) PCR Methods Applic., 2:318–322). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR is used to amplify or extend sequences using divergent primers based on a known region (Triglia et al. (1988) Nucleic Acids Res., 16:8186). The primers may be designed using Oligo 4.0 (National Biosciences Inc, Plymouth Minn.), or another appropriate program, to be, for example, 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template. In yet other embodiments of the present invention, capture PCR (Lagerstrom et al. (1991) PCR Methods Applic., 1: 111–119) is used. This is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR. In still other embodiments, walking PCR is utilized. Walking PCR is a method for targeted gene walking that permits retrieval of unknown sequence (Parker et al. (1991) Nucleic Acids Res., 19:3055–60). The PROMOTERFINDER kit (Clontech) uses PCR, nested primers and special libraries to "walk in" genomic DNA. This process avoids the need to screen libraries and is useful in finding intron/exon junctions. In yet other embodiments of the present invention, add TAIL PCR is used as a preferred method for obtaining flanking genomic regions, including regulatory regions (Lui and Whittier, (1995); Lui et al. (1995)).

Preferred libraries for screening for full-length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic libraries are useful for obtaining introns and extending 5' sequence.

It is contemplated that the methods described above are used to discover other AcDAGATs coding sequences and genes from plants that are known to possess AcTAGs. Exemplary plants include those from families Celastraceae, Lardizabalaceae, Rosaceae and Ranunculaceae.

V. Variants of Diacylglycerol Acetyltransferase

In some embodiments, the present invention provides isolated variants of the disclosed nucleic acid sequence encoding AcDAGAT, and the polypeptides encoded thereby; these variants include mutants, fragments, fusion proteins, or functional equivalents of AcDAGAT. Thus, nucleotide sequences of the present invention are engineered in order to alter an AcDAGAT coding sequence for a variety of reasons, including but not limited to alterations that modify the cloning, processing and/or expression of the gene product (such alterations include inserting new restriction sites, altering glycosylation patterns, and changing codon preference) as well as varying the enzymatic activity (such changes include but are not limited to differing substrate affinities, differing substrate preferences and utilization, differing inhibitor affinities or effectiveness, differing reaction kinetics, varying subcellular localization, and varying protein processing and/or stability). For example, mutations are introduced which alter the substrate specificity, such that the preferred substrate is changed.

In other embodiments, the present invention provides isolated nucleic acid sequences encoding an AcDAGAT, where the encoded acetyltransferase competes for binding to an unsaturated fatty acid substrate with a protein comprising the amino acid sequence of SEQ ID NO:2.

A. Mutants and Homologs of a Plant Diacylglycerol Acetyltransferase

Some embodiments of the present invention provide mutant forms of an AcDAGAT (in other words, muteins). In preferred embodiments, variants result from mutation, (in other words, a change in the nucleic acid sequence) and generally produce altered mRNAs or polypeptides whose structure or function may or may not be altered. Any given gene may have none, one, or many mutant forms. Common mutational changes that give rise to variants are generally ascribed to deletions, additions or substitutions of nucleic acids. Each of these types of changes may occur alone, or in combination with the others, and at the rate of one or more times in a given sequence.

Still other embodiments of the present invention provide isolated nucleic acid sequence encoding AcDAGAT homologs, and the polypeptides encoded thereby.

It is contemplated that is possible to modify the structure of a peptide having an activity (for example, a diacylglycerol acetyltransferase activity) for such purposes as increasing synthetic activity or altering the affinity of the AcDAGAT for a substrate, or for increasing stability or turnover or subcellular location of the polypeptide. Such modified peptides are considered functional equivalents of peptides having an activity of an AcDAGAT as defined herein. A modified peptide can be produced in which the nucleotide sequence encoding the polypeptide has been altered, such as by substitution, deletion, or addition.

In some preferred embodiments of the present invention, the alteration increases synthetic activity or alters the affinity of the AcDAGAT for a particular acetyl- or related group-CoA or acetyl or related group acceptor substrate. In particularly preferred embodiments, these modifications do not significantly reduce the synthetic activity of the modified enzyme. In other words, construct "X" can be evaluated in order to determine whether it is a member of the genus of modified or variant AcDAGAT of the present invention as defined functionally, rather than structurally. In preferred embodiments, the activity of variant AcDAGAT is evaluated by the methods described in the Examples. Accordingly, in some embodiments the present invention provides nucleic acids encoding an AcDAGAT that complement the coding region of SEQ ID NO: 1. In other embodiments, the present invention provides nucleic acids encoding an AcDAGAT that compete for the binding of diacylglycerol or acetyl substrates with the protein encoded by SEQ ID NO: 1.

In other preferred embodiments of the alteration, the alteration results in intracellular half-lives dramatically different from that of the corresponding wild-type protein. For example, an altered protein is rendered either more stable or less stable to proteolytic degradation or other cellular process that result in destruction of, or otherwise inactivate AcDAGAT. Such homologs, and the genes that encode them, can be utilized to alter the activity of AcDAGAT by modulating the half-life of the protein. For instance, a short half-life can give rise to more transient AcDAGAT biological effects. Other variants have characteristics which are either similar to wild-type AcDAGAT, or which differ in one or more respects from wild-type AcDAGAT.

As described above, mutant forms of an AcDAGAT are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (in other words, conservative mutations) will not have a major effect on the biological activity of the resulting molecule. Accordingly, some embodiments of the present invention provide variants of an AcDAGAT disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (for example, Stryer ed. (1981) *Biochemistry, pg.* 17–21, 2nd ed, WH Freeman and Co.). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (for example, replacement of a glycine with a tryptophan). Analogous minor variations can also include amino acid deletions or insertions, or both. Guidance in determining which amino acid residues can be substituted, inserted, or deleted without abolishing biological activity can be found using computer programs (for example, LASERGENE software, DNASTAR Inc., Madison, Wis.).

Mutants of an AcDAGAT can be generated by any suitable method well known in the art, including but not limited to site-directed mutagenesis, randomized "point" mutagenesis, and domain-swap mutagenesis in which portions of the *Euonymus* DAGAT cDNA are "swapped" with the analogous portion of other plant or bacterial DAGAT-encoding cDNAs (Back and Chappell (1996) PNAS 93: 6841–6845).

Variants may be produced by methods such as directed evolution or other techniques for producing combinatorial libraries of variants. Thus, the present invention further contemplates a method of generating sets of combinatorial mutants of the present AcDAGAT proteins, as well as truncation mutants, and is especially useful for identifying potential variant sequences (in other words, homologs) that possess the biological activity of an AcDAGAT of the present invention (for example, transfer of an acetyl or related group to diacylglycerol). In addition, screening such combinatorial libraries is used to generate, for example, novel AcDAGAT homologs that possess novel substrate specificities or other biological activities all together; examples of substrate specificities are described above.

It is contemplated that the AcDAGAT nucleic acids (for example, SEQ ID NO: 1, and fragments and variants thereof) can be utilized as starting nucleic acids for directed evolution. These techniques can be utilized to develop AcDAGAT variants having desirable properties such as increased synthetic activity or altered affinity for a particular acyl-CoA or acyl acceptor substrate.

In some embodiments, artificial evolution is performed by random mutagenesis (for example, by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech., 14, 458–67; Leung et al. (1989) Technique, 1:11–15; Eckert and Kunkel (1991) PCR Methods Appl., 1:17–24; Caldwell and Joyce (1992) PCR Methods Appl., 2:28–33; and Zhao and Arnold (1997) Nuc. Acids. Res., 25:1307–08). After mutagenesis, the resulting clones are selected for desirable activity (for example, screened for diacylglycerol acetyltransferase activity as described subsequently). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (for example, Smith (1994) Nature, 370:324–25; U.S. Pat. Nos. 5,837,458; 5,830,721; 5,811,238; 5,733,731). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer (1994) Nature, 370:398–91; Stemmer (1994) Proc. Natl. Acad. Sci. USA, 91, 10747–10751; Crameri et al. (1996) Nat. Biotech., 14:315–319; Zhang et al. (1997) Proc. Natl. Acad. Sci. USA, 94:4504–09; and Crameri et al. (1997) Nat. Biotech., 15:436–38). Variants produced by directed evolution can be screened for DAGAT activity by the methods described subsequently (see for example Example 2).

In some embodiments of a combinatorial mutagenesis approach of the present invention, the amino acid sequences of a population of AcDAGAT coding sequences are aligned, preferably to promote the highest homology possible. Such a population of variants can include, for example, AcDAGAT homologs from one or more species, or AcDAGAT homologs from the same species but which differ due to mutation. Amino acids that appear at each position of the aligned sequences are selected to create a degenerate set of combinatorial sequences.

In preferred embodiments of the present invention, the combinatorial AcDAGAT library is produced by way of a degenerate library of genes encoding a library of polypeptides that each include at least a portion of candidate AcDAGAT-protein sequences. For example, a mixture of synthetic oligonucleotides is enzymatically ligated into gene sequences such that the degenerate set of candidate AcDAGAT sequences are expressible as individual polypeptides, or alternatively, as a set of larger fusion proteins (for example, for phage display) containing the set of AcDAGAT sequences therein.

There are many ways by which the library of potential AcDAGAT homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential AcDAGAT sequences. The synthesis of degenerate oligonucleotides is well known in the art (See for example, Narang (1983) Tetrahedron Lett., 39:3–9; Itakura et al. (1981) Recombinant DNA, in Walton (ed.), Proceedings of the 3rd Cleveland Symposium on Macromolecules, Elsevier, Amsterdam, pp 273–289; Itakura et al. (1984) Annu. Rev. Biochem., 53:323; Itakura et al. (1984) Science 198:1056; Ike et al. (1983) Nucl. Acid Res., 11:477). Such techniques have been employed in the directed evolution of other proteins (See for example, Scott et al. (1980) Science, 249:386–390; Roberts et al. (1992) Proc. Natl. Acad. Sci. USA, 89:2429–2433; Devlin et al. (1990) Science, 249: 404–406; Cwirla et al. (1990) Proc. Natl. Acad. Sci. USA, 87: 6378–6382; as well as U.S. Pat. Nos. 5,223,409, 5,198,346, and 5,096,815).

B. Truncation Mutants of Plant Diacylglycerol Acetyltransferase

In addition, the present invention provides isolated nucleic acid sequences encoding fragments of AcDAGAT (in other words, truncation mutants), and the polypeptides encoded by such nucleic acid sequences. In preferred embodiments, the AcDAGAT fragment is biologically active.

In some embodiments of the present invention, when expression of a portion of an AcDAGAT protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol., 169:751–757) and *Salmonella typhimurium* and its in vitro activity has been demonstrated on recombinant proteins (Miller et al. (1990) Proc. Natl. Acad. Sci. USA, 84:2718–1722). Therefore, removal of an N-terminal methionine, if desired, can be achieved either in vivo by expressing such recombinant polypeptides in a host that produces MAP (for example, *E. coli* or CM89 or *S. cerevisiae*), or in vitro by use of purified MAP.

C. Fusion Proteins Containing Plant Diacylglycerol Acetyltransferase

The present invention also provides nucleic acid sequences encoding fusion proteins incorporating all or part of AcDAGAT, and the polypeptides encoded by such nucleic acid sequences. In some embodiments, the fusion proteins have an AcDAGAT functional domain with a fusion partner. Accordingly, in some embodiments of the present invention, the coding sequences for the polypeptide (for example, an AcDAGAT functional domain) is incorporated as a part of a fusion gene including a nucleotide sequence encoding a different polypeptide. In one embodiment, a single fusion product polypeptide transfers an acetyl group to diacylglycerol (one fusion partner possesses the ability to synthesize AcTAG).

In some embodiments of the present invention, chimeric constructs code for fusion proteins containing a portion of an AcDAGAT and a portion of another gene. In some embodiments, the fusion proteins have biological activity similar to the wild type AcDAGAT (for example, have at least one desired biological activity of AcDAGAT). In other embodiments, the fusion proteins have altered biological activity.

In other embodiments of the present invention, chimeric constructs code for fusion proteins containing an AcDAGAT gene or portion thereof and a leader or other signal sequences which direct the protein to targeted subcellular locations. Such sequences are well known in the art, and direct proteins to locations such as the chloroplast, the mitochondria, the endoplasmic reticulum, the tonoplast, the golgi network, and the plasmalemma.

In addition to utilizing fusion proteins to alter biological activity, it is widely appreciated that fusion proteins can also facilitate the expression and/or purification of proteins, such as an AcDAGAT protein of the present invention. Accordingly, in some embodiments of the present invention, an AcDAGAT is generated as a glutathione-S-transferase (in other words, GST fusion protein). It is contemplated that such GST fusion proteins enables easy purification of an AcDAGAT, such as by the use of glutathione-derivatized matrices (See for example, Ausabel et al. (eds.) (1991) Current Protocols in Molecular Biology, John Wiley & Sons, NY).

In another embodiment of the present invention, a fusion gene coding for a purification leader sequence, such as a poly-(His)/enterokinase cleavage site sequence at the N-terminus of the desired portion of an AcDAGAT allows purification of the expressed AcDAGAT fusion protein by affinity chromatography using a $Ni^{2+}$ metal resin. In still another embodiment of the present invention, the purification leader sequence is then subsequently removed by treatment with enterokinase (See for example, Hochuli et al. (1987) J. Chromatogr., 411:177; and Janknecht et al. Proc. Natl. Acad. Sci. USA, 88:8972). In yet other embodiments of the present invention, a fusion gene coding for a purification sequence appended to either the N (amino) or the C (carboxy) terminus allows for affinity purification; one example is addition of a hexahistidine tag to the carboxy terminus of an AcDAGAT, which is contemplated to be useful for affinity purification.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See for example, Current Protocols in Molecular Biology, supra). In yet other embodiments of the present invention, epitope tags of AcDAGAT are prepared. Epitope tags are prepared as described by Lin et al., who epitope tagged a human ACAT, which is in the same gene family as DAGAT. The epitope tags were single HA tags internally, at 12 well distributed sites along the polypeptide, and a C-terminal his tag, and the protein retained full or partial activity with these tags.

D. Screening Gene Products

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of AcDAGAT homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in one embodiment of the present invention, the candidate AcDAGAT gene products are displayed on the surface of a cell or viral particle, and the ability of particular cells or viral particles to synthesize AcTAGs is assayed using the techniques described in the Examples. In other embodiments of the present invention, the gene library is cloned into the gene for a surface membrane protein of a bacterial cell, and the resulting fusion protein detected by panning (WO 88/06630; Fuchs et al. (1991) BioTechnol., 9:1370–1371; and Goward et al. (1992) TIBS 18:136–140). In other embodiments of the present invention, fluorescently labeled molecules that bind AcDAGAT can be used to score for potentially functional AcDAGAT homologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (See for example, WO 90/02909; WO 92/09690; Marks et al. (1992) J. Biol. Chem., 267:16007–16010; Griffths et al. (1993) EMBO J., 12:725–734; Clackson et al. (1991) Nature, 352:624–628; and Barbas et al. (1992) Proc. Natl. Acad. Sci., 89:4457–4461).

In another embodiment of the present invention, the recombinant phage antibody system (for example, RPAS, Pharmacia Catalog number 27-9400-01) is modified for use in expressing and screening of AcDAGAT combinatorial libraries. The pCANTAB 5 phagemid of the RPAS kit contains the gene that encodes the phage gil coat protein. In some embodiments of the present invention, the AcDAGAT combinatorial gene library is cloned into the phagemid adjacent to the gIII signal sequence such that it is expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate AcDAGAT gene insert. The resulting recombinant phage contain phagemid DNA encoding a specific candidate AcDAGAT-protein and display one or more copies of the corresponding fusion coat protein. In some embodiments of the present invention, the phage-displayed candidate proteins that are capable of, for example, metabolizing a hydroperoxide, are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning will greatly enrich for AcDAGAT homologs, which can then be screened for further biological activities in order to differentiate agonists and antagonists.

In light of the present disclosure, other forms of mutagenesis generally applicable will be apparent to those skilled in the art in addition to the aforementioned rational mutagenesis based on conserved versus non-conserved residues. For example, AcDAGAT homologs can be generated and screened using, for example, alanine scanning mutagenesis and the like (Ruf et al. (1994) Biochem., 33:1565–1572; Wang et al. (1994) J. Biol. Chem., 269:3095–3099; Balint (1993) Gene 137:109–118; Grodberg et al. (1993) Eur. J. Biochem., 218:597–601; Nagashima et al. (1993) J. Biol. Chem., 268:2888–2892; Lowman et al. (1991) Biochem., 30:10832–10838; and Cunningham et al. (1989) Science, 244:1081–1085), by linker scanning mutagenesis (Gustin et al. (1993) Virol., 193:653–660; Brown et al. (1992) Mol. Cell. Biol., 12:2644–2652; McKnight et al. Science, 232: 316); or by saturation mutagenesis (Meyers et al. (1986) Science, 232:613).

VI. Expression of Cloned Diacylglycerol Acetyltransferase

In other embodiment of the present invention, nucleic acid sequences corresponding to the AcDAGAT genes, homologs and mutants as described above may be used to generate recombinant DNA molecules that direct the expression of the encoded protein product in appropriate host cells.

As will be understood by those of skill in the art, it may be advantageous to produce AcDAGAT-encoding nucleotide sequences possessing non-naturally occurring codons. Therefore, in some preferred embodiments, codons preferred by a particular prokaryotic or eukaryotic host (Murray et al. (1989) Nucl. Acids Res., 17) can be selected, for example, to increase the rate of AcDAGAT expression or to produce recombinant RNA transcripts having desirable properties, such as a longer half-life, than transcripts produced from naturally occurring sequence.

A. Vectors for Production of Plant Diacylglycerol Acetyltransferase

The nucleic acid sequences of the present invention may be employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (for example, derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic acid sequences as broadly described above (for example, SEQ ID NO: 1). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, a nucleic acid sequence of the present invention within an expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (for example, dihydrofolate reductase or neomycin resistance for eukaryotic cell culture, or tetracycline or ampicillin resistance in *E. coli*).

In some embodiments of the present invention, transcription of the DNA encoding polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of Plant Diacylglycerol Acetyltransferase

In a further embodiment, the present invention provides host cells containing any of the above-described constructs. In some embodiments of the present invention, the host cell is a higher eukaryotic cell (for example, a plant cell). In other embodiments of the present invention, the host cell is a lower eukaryotic cell (for example, a yeast cell). In still other embodiments of the present invention, the host cell can be a prokaryotic cell (for example, a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman (1981) Cell 23:175), 293T, C127, 3T3, HeLa and BHK cell lines, NT-1 (tobacco cell culture line), root cell and cultured roots in rhizosecretion (Gleba et al. (1999) Proc Natl Acad Sci USA 96: 5973-5977). Other examples include microspore-derived cultures of oilseed rape (Weselake R J and Taylor D C (1999) Prog. Lipid Res. 38: 401), and transformation of pollen and microspore culture systems. Further examples are described in the Examples.

The constructs in host cells can be used in a conventional manner to produce the gene product encoded by any of the recombinant sequences of the present invention described above. In some embodiments, introduction of the construct into the host cell can be accomplished by calcium phosphate transfection, DEAE-Dextran mediated transfection, or electroporation (See for example, Davis et al. (1986) Basic Methods in Molecular Biology). Alternatively, in some embodiments of the present invention, a polypeptide of the invention can be synthetically produced by conventional peptide synthesizers.

Proteins can be expressed in eukaryotic cells, yeast, bacteria, or other cells under the control of appropriate promoters. Cell-free translation systems can also be employed to produce such proteins using RNAs derived from a DNA construct of the present invention. Appropriate cloning and expression vectors for use with prokaryotic and eukaryotic hosts are described by Sambrook, et al. (1989) *Molecular Cloning: A Laboratory Manual*, Second Edition, Cold Spring Harbor, N.Y.

In some embodiments of the present invention, following transformation of a suitable host strain and growth of the host strain to an appropriate cell density, the selected promoter is induced by appropriate means (for example, temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

VII. Production of Acetyl Glycerides

In one aspect of the present invention, methods are provided for producing acetyl glycerides (AcTAGs). Although the following methods are described in terms of production of AcTAGs, it is understood that these methods are also applicable to an AcDAGAT that transfers a related group, resulting in production of TAGs to which the group related to acetyl is transferred. In some embodiments, AcTAGs are produced in vivo, in organisms transformed with a heterologous gene encoding a polypeptide exhibiting diacylglycerol acetyltransferase activity and grown under conditions sufficient to effect production of AcTAGs. In other embodiments, AcTAGs are produced in vitro, from either nucleic acid sequences encoding an AcDAGAT of the present invention or from polypeptides exhibiting diacylglycerol acetyltransferase activity.

A. Novel TAGs

By controlling the type of substrate, it is possible to produce novel TAGs. For example, the results from expression of *Euonymus* AcDAGAT (EaDAGAT) in yeast cells (as described in Example 4) demonstrate that a triacylglycerol species acetyldipalmitolein was produced; this triacylglycerol species has not been previously reported, and is therefore novel. It is further contemplated that the use of the EaDAGAT can be used to produce structures such as acetyldiricinolein; acetyldivernolin, or acetyldicaprin; these structures also have not been previously reported, and are therefore novel.

In some embodiments, novel compounds are produced by incubating a EaDAGAT enzyme with acetyl-CoA and the appropriate DAG substrate (for example, diricinolein or divernolin) under suitable conditions such that the AcTAG products are synthesized. In other embodiments, novel compounds are produced by incubating a EaDAGAT enzyme with a DAG substrate and an appropriate related group-CoA (for example, cinnamoyl) under suitable conditions such that the AcTAG products are synthesized. It is contemplated that cinnamoyl-TAG will absorb UV and can be used in sunscreens. Exemplary suitable conditions for incubations are described below and in the Examples for DAGAT assays.

Such compounds can be produced in vivo by transforming a plant in which the appropriate DAG substrate is present with a gene encoding EaDAGAT under control of a suitable promoter (as for example is described in Example 5), such that EaDAGAT is expressed when and where the appropriate DAG substrate is synthesized, resulting in the synthesis of AcTAG.

B. In Vivo Production in Transgenic Organism

In some embodiments of the present invention, AcTAGs are produced in vivo, by providing an organism transformed with a heterologous gene encoding an AcDAGAT of the present invention and growing the transgenic organism under conditions sufficient to effect production of AcTAGs. In other embodiments of the present invention, AcTAGs are produced in vivo by transforming an organism with a heterologous gene encoding an AcDAGAT of the present invention and growing the transgenic organism under conditions sufficient to effect production of AcTAGs. Illustrative examples of transgenic organisms are described below and provided in the Examples.

Organisms which are transformed with a heterologous gene encoding an AcDAGAT of the present invention include preferably those which naturally synthesize and store in some manner triacylglycerols (TAGs), and those which are commercially feasible to grow and suitable for harvesting large amounts of the TAG products. Such organisms include but are not limited to, oleaginous yeast and algae, and plants and animals. Examples of yeasts include oleaginous yeast, which include but are not limited to the genera Lipomyces, *Candida, Rhodotorula, Rhodosporidium* and *Cryptococcus*, which can be grown in commercial-scale fermenters. Examples of plants include preferably oil-producing plants, such as soybean, rapeseed and canola, sunflower, cotton, corn, cocoa, safflower, oil palm, coconut palm, flax, castor, and peanut. Many commercial cultivars can be transformed with heterologous genes. In cases where that is not possible, non-commercial cultivars of plants can be transformed, and the trait for expression of AcDAGAT of the present invention moved to commercial cultivars by breeding techniques well-known in the art.

A heterologous gene encoding an AcDAGAT of the present invention, which includes variants of an AcDAGAT, includes any suitable sequence of the invention as described above. Preferably, the heterologous gene is provided within an expression vector such that transformation with the vector results in expression of the polypeptide; suitable vectors are described above and following.

A transgenic organism is grown under conditions sufficient to effect production of AcTAGs. In some embodiments of the present invention, a transgenic organism is supplied with exogenous substrates of the AcDAGAT (as, for example, in a fermenter). Such substrates can comprise sugars as carbon sources for TAG synthesis, fatty acids and glycerol used directly for the production of DAG and TAG, DAG itself, and acetic acid which will both provide a general carbon source and be used for the production of acetyl-CoA and/or diacylglycerols (DAGs). When related groups are transferred to DAG, such substrates may instead or in addition be provided to the transgenic organism; exemplary related group include but are not limited to butyrate, propionate, and cinnamate. Substrates may be supplied in various forms as are well known in the art; such forms include aqueous suspensions prepared by sonication, aqueous suspensions prepared with detergents and other surfactants, dissolution of the substrate into a solvent, and dried powders of substrates. Such forms may be added to organisms or cultured cells or tissues grown in fermenters.

In yet other embodiments of the present invention, a transgenic organism comprises a heterologous gene encoding an AcDAGAT of the present invention operably linked to an inducible promoter, and is grown either in the presence of the an inducing agent, or is grown and then exposed to an inducing agent. In still other embodiments of the present invention, a transgenic organism comprises a heterologous gene encoding an AcDAGAT of the present invention operably linked to a promoter which is either tissue specific or developmentally specific, and is grown to the point at which the tissue is developed or the developmental stage at which the developmentally-specific promoter is activated. Such promoters include seed specific promoters.

In alternative embodiments, a transgenic organism as described above is engineered to produce greater amounts of the diacylglycerol substrate. Thus, it is contemplated that a transgenic organism may include further modifications such that fatty acid synthesis is increased, and may in addition or instead include exogenous acyltransferases and/or phosphatidic acid phospatases.

In other embodiments of the present invention, a host organism produces large amounts of a desired substrate, such as acetyl-CoA or DAG; non-limiting examples include organisms transformed with genes encoding acetyl-CoA synthetases and/or ATP citrate lyase. In some embodiments, it is contemplated that certain DAGs will result in the synthesis of novel AcTAGs with desirable properties. Thus, a particularly suitable host is one which produces a high proportion of such a DAG.

In other embodiments, a host organism produces low amounts of a desired substrate such as DAG. It is contemplated that in such hosts, novel TAGs produced from an exogenous AcDAGAT are a higher proportion of the total TAGs; advantages include less expensive purification of the novel TAGs. Non-limiting exemplary hosts include those with low flux through lipid synthetic systems or with low endogenous DAGAT activity (either or both DAGAT1 or DAGAT2). Such hosts may occur naturally or via genetic engineering techniques. Non-limiting exemplary techniques include knock-out produced by EMS and transposon tagging.

In other embodiments of the present invention, the methods for producing AcTAGs further comprise collecting the AcTAGs produced. Such methods are known generally in the art, and include harvesting the transgenic organisms and extracting the AcTAGs (see, for example, Christie, W. W. (1982) *Lipid Analysis, 2nd Edition* (Pergamon Press, Oxford); and Kates, M (1986) *Techniques of Lipidology* (Elsevier, Amsterdam)). Extraction procedures preferably include solvent extraction, and typically include disrupting cells, as by chopping, mincing, grinding, and/or sonicating, prior to solvent extraction. In one embodiment, lipids are extracted from the tissue according to the method of Bligh and Dyer (1959) (Can J Biochem Physiol 37: 911–917). In yet other embodiments' of the present invention, the AcTAGs are further purified, as for example by thin layer liquid chromatography, gas-liquid chromatography, counter current chromatography or high performance liquid chromatography.

1. Transgenic Plants, Seeds, and Plant Parts

Plants are transformed with at least a heterologous gene encoding an AcDAGAT of the present invention according to procedures well known in the art. It is contemplated that the heterologous gene is utilized to increase the level of the enzyme activities encoded by the heterologous gene.

a. Plants

The methods of the present invention are not limited to any particular plant. Indeed, a variety of plants are contemplated, including but not limited to tomato, potato, tobacco, pepper, rice, corn, barley, wheat, *Brassica, Arabidopsis*, sunflower, soybean, poplar, and pine. Preferred plants include oil-producing species, which are plant species which produce and store triacylglycerol in specific organs, primarily in seeds. Such species include but are not limited to soybean (*Glycine max*), rapeseed and canola (including *Brassica napus* and *B. campestris*), sunflower (*Helianthus* annus), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species undergoing domestication, such as *Vernonia* and *Cuphea*, which may be a source of unique fatty acids. In addition plant lines where the endogenous DAGAT gene(s) has been inactivated by any method, but including mutagenesis (Katavic et al, 1995 and Zou et al. (1999), transposon tagging (Routaboul et al., 1999), hairpin RNA (Stoutjesdijk et al. (2002) Plant Physiol. 129: 1723; Liu et al. (2002) Plant Physiol. 129: 1732) and chimeraplasty (Beetham et al. (1999) Proc. Natl. Acad. Sci. USA 96: 8774; Zhu et al. (2000) Nat. Biotechnol. 18: 555) are considered ideal for optimum expression of the *Euonymus* DAGAT gene. In addition lines where DAGAT genes from other gene families and other routes to TAG such as PDAT have been down regulated are contemplated.

b. Vectors

The methods of the present invention contemplate the use of at least a heterologous gene encoding an AcDAGAT of the present invention, as described above.

Heterologous genes intended for expression in plants are first assembled in expression cassettes comprising a promoter. Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See for example, Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.).

In general, these vectors comprise a nucleic acid sequence of the invention encoding an AcDAGAT of the present invention (as described above) operably linked to a promoter and other regulatory sequences (for example, enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter $^{35}$S of cauliflower mosaic virus; a wound-inducible promoter from tomato, leucine amino peptidase ("LAP," Chao et al. (1999) Plant Physiol 120: 979–992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267); a tetracycline-inducible promoter (U.S. Pat. No. 5,057,422); and seed-specific promoters, such as those for seed storage proteins (for example, phaseolin, napin, oleosin, and a promoter for soybean beta conglycin (Beachy et al. (1985) EMBO J. 4: 3047–3053)). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV $^{35}$S terminator, the tml terminator, the pea rbcS E9 terminator, and the nopaline and octopine synthase terminator (See for example, Odell et al. (1985) Nature 313:810; Rosenberg et al. (1987)

Gene, 56:125; Guerineau et al. (1991) Mol. Gen. Genet., 262:141; Proudfoot (1991) Cell, 64:671; Sanfacon et al. Genes Dev., 5:141; Mogen et al. (1990) Plant Cell, 2:1261; Munroe et al. (1990) Gene, 91:151; Ballad et al. (1989) Nucleic Acids Res. 17:7891; Joshi et al. (1987) Nucleic Acid Res., 15:9627).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adhl gene have been found to significantly enhance the expression of the wild-type gene under its cognate promoter when introduced into maize cells (Calais et al. (1987) Genes Develop. 1: 1183). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Calderone et al. (1984) Cell 39:499; Lassoer et al. (1991) Plant Molecular Biology 17:229), a plant translational consensus sequence (Joshi (1987) Nucleic Acids Research 15:6643), an intron (Luehrsen and Walbot (1991) Mol. Gen. Genet. 225:81), and the like, operably linked to the nucleic acid sequence encoding AcDAGAT.

In preparing a construct comprising a nucleic acid sequence encoding AcDAGAT of the present invention, various DNA fragments can be manipulated, so as to provide for the DNA sequences in the desired orientation (for example, sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (for example, transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18:1062; Spencer et al. (1990) Theor. Appl. Genet. 79:625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an *Agrobacterium* mediated transfection process (See for example, U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention are utilized to construct vectors derived from plant (+) RNA viruses (for example, brome mosaic virus, tobacco mosaic virus, alfalfa mosaic virus, cucumber mosaic virus, tomato mosaic virus, and combinations and hybrids thereof). Generally, the inserted AcDAGAT polynucleotide of the present invention can be expressed from these vectors as a fusion protein (for example, coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV $^{35}$S promoter in operational fusion to the *E. coli* GUS gene and the CaMV $^{35}$S transcriptional terminator (WO 93/07278).

c. Transformation Techniques

Once a nucleic acid sequence encoding an AcDAGAT of the present invention is operatively linked to an appropriate promoter and inserted into a suitable vector for the particular transformation technique utilized (for example, one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See for example, U.S. Pat. Nos. 5,451,513; 5,545,817; 5,545,818; PCT application WO 95/16783). The basic technique for chloroplast transformation involves introducing regions of cloned plastid DNA flanking a selectable marker together with the nucleic acid encoding the RNA sequences of interest into a suitable target tissue (for example, using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. (1990) PNAS, 87:8526; Staub and Maliga, (1992) Plant Cell, 4:39). The presence of cloning sites between these markers allowed creation of a plastid targeting vector introduction of foreign DNA molecules (Staub and Maliga (1993) EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179). In still other embodiments, the vector is transferred into the plant cell by using polyethylene glycol (Krens et al. (1982) Nature, 296:72; Crossway et al. (1986) BioTechniques, 4:320); fusion of protoplasts with other entities, either minicells, cells, lysosomes or other fusible lipid-surfaced bodies (Fraley et al. (1982) Proc. Natl. Acad. Sci., USA, 79:1859); protoplast transformation (EP 0 292 435); direct gene transfer (Paszkowski et al. (1984) EMBO J., 3:2717; Hayashimoto et al. (1990) Plant Physiol. 93:857).

In still further embodiments, the vector may also be introduced into the plant cells by electroporation (Fromm, et al. (1985) Proc. Natl. Acad. Sci. USA 82:5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (for example, available from Agracetus, Inc., Madison, Wis. and Dupont, Inc., Wilmington, Del.). (See for example, U.S. Pat. No. 4,945,050; and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al. (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat).

In addition to direct transformation, in some embodiments, the vectors comprising a nucleic acid sequence encoding an AcDAGAT of the present invention are transferred using *Agrobacterium*-mediated transformation (Hinchee et al. (1988) Biotechnology, 6:915; Ishida et al. (1996) Nature Biotechnology 14:745). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (for example, nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237: 1176). Species that are susceptible infection by *Agrobacterium* may be transformed in vitro. Alternatively, plants may be transformed in vivo, such as by transformation of a whole plant by *Agrobacteria* infiltration of adult plants, as in a "floral dip" method (Bechtold N, Ellis J, Pelletier G (1993) Cr. Acad. Sci. III-Vie 316: 1194–1199).

d. Regeneration

After selecting for transformed plant material that can express the heterologous gene encoding an AcDAGAT of the present invention, whole plants are regenerated. Plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. 1 (1984), and Vol. III (1986). It is known that many plants can be regenerated from cultured cells or tissues, including but not limited to all major species of sugarcane, sugar beet, cotton, fruit and other trees, legumes and vegetables, and monocots (for example, the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

e. Generation of Transgenic Lines

Transgenic lines are established from transgenic plants by tissue culture propagation. The presence of nucleic acid sequences encoding a heterologous AcDAGAT of the present invention (including mutants or variants thereof) may be transferred to related varieties by traditional plant breeding techniques.

These transgenic lines are then utilized for evaluation of oil production and other agronomic traits.

C. In Vitro Systems

In other embodiments of the present invention, AcTAGs are produced in vitro, from either nucleic acid sequences encoding an AcDAGAT of the present invention or from polypeptides exhibiting a diacylglycerol acetyltransferase activity.

1. Using Nucleic Acid Sequences Encoding Diacylglycerol Acetyltransferase

In some embodiments of the present invention, methods for producing AcTAGs comprise adding an isolated nucleic acid sequence encoding an AcDAGAT of the present invention to in vitro expression systems under conditions sufficient to cause production of AcTAGs. The isolated nucleic acid sequence encoding a plant acetyltransferase is any suitable sequence of the invention as described above, and preferably is provided within an expression vector such that addition of the vector to an in vitro transcription/translation system results in expression of the polypeptide. Furthermore, the system contemplated is specific for the translation and function of eukaryotic membrane proteins, that is, it is a microsomal system. The system further comprises the substrates for AcDAGAT, as previously described. Alternatively, the system further comprises the means for generating the substrates for an AcDAGAT of the present invention. Such means include but are not limited to those previously described.

In other embodiments of the present invention, the methods for producing large quantities of AcTAGs further comprise collecting the AcTAGs produced. Such methods are known generally in the art, and described briefly above. In yet other embodiments of the present invention, the AcTAGs are further purified, as for example by thin layer liquid chromatography, gas-liquid chromatography, high pressure liquid chromatography, crystallization and/or vacuum distillation.

2. Using Diacylglycerol Acetyltransferase Polypeptides

In some embodiments of the present invention, methods for producing large quantities of AcTAGs comprise incubating an AcDAGAT of the present invention under conditions sufficient to result in the synthesis of AcTAGs; generally, such incubation is carried out in a mixture that comprises the AcDAGAT.

An AcDAGAT of the present invention, as described above, is obtained by purification of either naturally occurring AcDAGAT or recombinant AcDAGAT from an organism transformed with heterologous gene encoding an AcDAGAT, as described above. A source of naturally occurring AcDAGAT is contemplated to include but not limited to plants, as for example *Euonymus*, or other members of the plant family Celastraceae, and in addition in the families Lardizabalaceae, Ranunculaceae and Rosaceae. A source of recombinant AcDAGAT is either plant, bacterial or other transgenic organisms, transformed with heterologous gene encoding AcDAGAT of the present invention, as described above. The recombinant AcDAGAT may include means for improving purification, as for example a 6×-His tag added to the C-terminus of the protein as described above. Alternatively, AcDAGAT is chemically synthesized.

The incubation mixture further comprises the substrates for AcDAGAT, as described above. Alternatively, the mixture further comprises the means for generating the substrates for AcDAGAT, such as the use of ATP-citrate lyase to generate acetyl-CoA from citrate or acetyl-CoA synthetase to generate acetyl-CoA from acetate, and phosphatidic acid phosphatase to generate diacylglycerol from phosphatidic acid or phospholipase C to generate diacylglycerol from phospholipids.

In other embodiments of the present invention, the methods for producing AcTAGs further comprise collecting the AcTAGs produced; such methods are described above.

VIII. Manipulation of Diacylglycerol Acetyltransferase Activity in Plants

It is further contemplated that the nucleic acids encoding an AcDAGAT of the present invention may be utilized to either increase or decrease the level of AcDAGAT mRNA and/or protein in transfected cells as compared to the levels in wild-type cells. Such transgenic cells have great utility, including but not limited to further research as to the effects of the overexpression of AcDAGAT, and as to the effects as to the underexpression or lack of AcDAGAT.

Accordingly, in some embodiments, expression in plants of nucleic acid sequences encoding an AcDAGAT of the present invention by the methods described above leads to the overexpression of AcDAGAT in transgenic plants, plant tissues, or plant cells.

In other embodiments of the present invention, the ACDAGAT polynucleotides are utilized to decrease the level of AcDAGAT protein or mRNA in transgenic plants, plant tissues, or plant cells as compared to wild-type plants, plant tissues, or plant cells. One method of reducing AcDAGAT expression utilizes expression of antisense transcripts. Antisense RNA has been used to inhibit plant target genes in a tissue-specific manner (for example, van der Krol et al. (1988) Biotechniques 6:958–976). Antisense inhibition has been shown using the entire cDNA sequence as well as a partial cDNA sequence (for example, Sheehy et al. (1988) Proc. Natl. Acad. Sci. USA 85:8805–8809; Cannon et al. (1990) Plant Mol. Biol. 15:39–47). There is also evidence that 3' non-coding sequence fragment and 5' coding sequence fragments, containing as few as 41 base-pairs of a 1.87 kb cDNA, can play important roles in antisense inhibition (Ch'ng et al. (1989) Proc. Natl. Acad. Sci. USA 86:10006–10010).

Accordingly, in some embodiments, an AcDAGAT encoding-nucleic acid of the present invention (for example, SEQ ID NO: 1, and fragments and variants thereof) are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff, et al. (1988) Nature 334:585–591. Ribozymes targeted to the mRNA of a lipid biosynthetic gene, resulting in a heritable increase of the target enzyme substrate, have also been described (Merlo A O et al. (1998) Plant Cell 10: 1603–1621).

Another method of reducing AcDAGAT expression utilizes the phenomenon of cosuppression or gene silencing (See for example, U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (for example, Napoli et al. (1990) Plant Cell 2:279–289; van der Krol et al. (1990) Plant Cell 2:291–299; Smith et al. (1990) Mol. Gen. Genetics 224:477–481). Accordingly, in some embodiments the nucleic acid sequences encoding an AcDAGAT of the present invention (for example including SEQ ID NOs 1, and fragments and variants thereof) are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

An effective method to down regulate a gene is by hairpin RNA constructs. Guidance to the design of such constructs for efficient, effective and high throughput gene silencing have been described (Wesley S V et al. (2001) Plant J. 27: 581–590). Another method to decrease expression of a gene (either endogenous or exogenous) is via siRNAs. siRNAs can be applied to a plant and taken up by plant cells; alternatively, siRNAs can be expressed in vivo from an expression cassette. Exemplary techniques for lipid gene antisense using hairpin RNA include Stoutjesdijk et al. (2002) Plant Physiol. 129: 1723; Liu et al. (2002) Plant Physiol. 129: 1732).

An advantage of siRNAs is the short length of the mRNA that is targeted; this allows preferential targeting of a first sequence that is very similar to a second sequence, while allowing expression of the second, non-targeted sequence. Thus, it is contemplated that AcDAGAT is specifically targeted, but not DAGAT, which would allow expression of DAGAT to be expressed.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); 1 or L (liters); ml (milliliters); μl (microliters); cm (centimeters); mm (millimeters); μm (micrometers); nm (nanometers); ° C. (degrees Centigrade); PCR (polymerase chain reaction); RT-PCR (reverse-transcriptase-PCR); TAIL-PCR (thermal asymmetric interlaced-PCR); RACE (Rapid Amplification of cDNA Ends); EST, expressed sequence tag; BLAST (Basic Local Alignment Search Tool); C16, C18, etc (fatty acyl group designation by number of carbon atoms in acyl chain); DAG (diacylglycerol); TAG (triacylglycerol); AcTAG (1,2-diacyl-3-acetins); LcTAG (long chain triacylglycerols); PC (phosphatidylcholine); DAGAT (diacylglycerol acyltransferase); diacylglycerol acetyltransferase (AcDAGAT); FAME (fatty acid methyl ester); GC/MS (gas chromatography/mass spectrometry); TLC (thin layer chromatography); FID (flame ionization detection/detector); SC medium (*Saccharomyces cerevisiae* medium); NT medium (*Nicotiana tabaccum* medium); MES (2-(N-morpholino)ethanesulphonic acid); hepes (N-2-hydroxyethylpiperazine-N'-2-ethanesulphonic acid); 2,4-D (2,4-dichlorophenoxyacetic acid); CFH (cell free homogenate); MSU (Michigan State University).

EXAMPLE 1

Experimental Plant Biochemistry Procedures

A. Materials

Developing Seeds

*Euonymus alata* developing seeds were collected from bushes on the Michigan State University campus, courtesy of the WJ Beal Garden and Campus Woody Plants. Seed capsules were harvested from mid-August through November. Seeds were removed from the capsule and from their yellowish-orange pericarp. Some fresh seeds were halved and used immediately for in vivo labeling experiments. For other seeds, the seed coats were removed and the cotyledons and embryos were either immediately used for the preparation of enzyme extracts or frozen in liquid nitrogen and stored at −80° C. for subsequent RNA extraction, for the preparation of cell free extracts for enzymology, or for lipids analysis.

RadioChemicals

[1-$^{14}$C]Acetate was purchased from American Radiolabeled Chemicals, Inc., while [1-$^{14}$C]acetyl-CoA, [1-$^{14}$C] palmitoyl-CoA and [1-$^{14}$C]oleoyl-CoA were purchased from New England Nuclear. Specific activities were 50–60 Ci/mol. [1-$^{14}$C]Acetyl-CoA was also prepared from [1-$^{14}$C] acetate using acetyl-CoA synthetase.

B. Radiolabeling of Developing *Euonymus* Seeds

Incubations contained 7–10 halved seeds, but no more than 200 mg fresh weight of tissue. Each assays contained 10 μCi of [1-$^{14}$C] acetic acid. Assays were run in 25 mM NaMES buffer, pH 6.0, with 25 mM sucrose and 0.4 M sorbitol osmoticum, and in a total volume of 1.0 ml. Assays were run for the time specified, at 28° C., with vigorous agitation to assist oxygenation of the medium. Assays were terminated by rapidly washing the tissue twice with distilled water to remove labeled substrate and then immediately heated at 90° C. in isopropanol for 5 minutes to inactivate enzymes (and particularly an endogenous phospholipase D activity) prior to lipid extraction. Lipids were extracted from the inactivated, homogenized seed tissue with hexane-isopropanol, as described by Hara and Radin (1978). An aliquot of the heptane-soluble [$^{14}$C]lipids was assayed for radioactivity by liquid scintillation counting.

C. Plant Enzyme Preparation and DAGAT Assays

All procedures were carried out on ice or at 4° C. Frozen embryo and endosperm tissue was added to two volumes of chilled buffer containing 0.3 M sucrose, 10 mM NaF, 5 mM $MgCl_2$, 2 mM dithiothreitol, 1 mM EDTA and 40 mM Hepes-NaOH (pH 7.4), homogenized, and filtered through two layers of Miracloth. The residue was rehomogenized in two more volumes of buffer and filtered. The filtrates were combined and constitute the cell free homogenate (CFH). The CFH was frozen and stored at −70° C. until used and typically contained 12–17 mg protein/ml. Protein concentrations were estimated using the Bio-Rad protein assay, which is based on the Bradford method (1976), using bovine serum albumin as the standard.

The standard (Ac)DAGAT assay contained [1-$^{14}$C]acetyl-CoA (100 μM, 200,000 d.p.m.) plus 140 μl of homogenization buffer in a total volume of 200 μl. 1,2-dioleoyl-sn-glycerol (50 μg, 0.4 mM) was added as 1 μl of ethanol solution. The assay was initiated by adding 20 μl of CFH. The reaction was run at room temperature (25° C.) for 15 min and terminated by the addition of hot isopropanol (1 ml). Lipids were extracted with hexane and isopropanol as described by Hara and Radin (1978). The [$^{14}$C]lipid residue was dissolved in hexane and an aliquot assayed for radioactivity by liquid scintillation counting. The standard long-chain DAGAT assay contained 20 μM [1-$^{14}$C]palmitoyl-CoA and 20–40 μl of CFH and was run for 30 minutes: all other aspects were as for acetyl DAGAT assays.

D. Lipid Analysis

To determine total lipid accumulation during *Euonymus* seed development, dried seeds were extracted with hexane-isopropanol according to Hara and Radin (1978) and the oil weighed. To determine individual lipid classes, internal standards, namely triheptadecanoin and dipentadecanoyl phosphatidylcholine, were added to an aliquot of total lipids. The lipid classes were isolated by preparative TLC. Transmethylation of the total lipids and of the lipid classes was accomplished by heating in sulphuric acid-methanol-toluene (5:95:25 v/v/v) for one hour at 80° C. The lipid classes recovered after preparative TLC were transmethylated directly on the silica, with methyl nonadecanoate added to each fraction for relative quantifications. GLC analysis of fatty acid methyl esters was accomplished using a 50 m×0.25 mm CP-Sil88 column temperature programmed from 150° C. to 220° C., with FID.

For analysis of triacylglycerols in different tissues of *Euonymus*, internal standards of triheptadecanoin and acetyldipentadecanoin were added to tissue lipid extracts. Long-chain triacylglycerols and acetylglycerides were then isolated by preparative TLC and analyzed by high temperature GC using a 30 m×0.25 mm DB-5ht column, temperature programmed from 250 to 360° C., with FID. Aliquots of the sample were also transmethylated for quantification of total fatty acids.

TLC analysis of unlabeled and labeled lipid classes was conducted using K6 silica plates (Whatman). 80/20/1 (v/v/v) Hexane/diethyl ether/acetic acid was used for analysis of triacylglycerols; 80/10/10/0.4 (v/v/v/v) toluene/ethyl ether/ethyl acetate/acetic acid was used for analysis of diacylglycerols; and 65/25/4 chloroform/methanol/water (v/v/v), 65/25/4 (v/v/v) chloroform/methanol/28% aqueous ammonium hydroxide and/or 85/15/5/2 (v/v/v/v) chloroform/methanol/acetic acid/water were used for analysis of polar lipids. Reverse phase analysis of triacylglycerols was carrier out using KC18F TLC plates developed with 3:1 (v/v) acetone:acetonitrile or 100% methanol. Silver nitrate TLC used silica TLC plates impregnated with 15% (w/v) silver nitrate in acetonitrile and developed three times with toluene at −15° C. After development of the TLC plates in the above solvent systems, radioactivity in bands was quantitated with a Packard Instant Imager.

For analysis of lipid classes recovered from TLC plates after in vivo labeling experiments, the transmethylation method of Ichihara et al. (1996) was employed. This derivatization, run at room temperature with sodium hydroxide/methanol/heptane, can be performed with quantitative recovery of [$^{14}$C] long-chain fatty acid methyl esters and complete loss of [$^{14}$C] acetyl groups (primarily as methyl acetate). When the [$^{14}$C] heptane-soluble material recovered from the transmethylation is analyzed by TLC, the contribution from [$^{14}$C] long-chain fatty acid methyl esters can be measured, and hence the amount of [$^{14}$C] long-chain fatty acids in the original [$^{14}$C] lipid determined. The use of transmethylation with complete loss of labeled methyl acetate and recovery of long-chain fatty acid methyl esters was also used to quantify the distribution of label between acetyl and long-chain acyl groups in isolated [$^{14}$C]3-acetyl-1,2-long-chain diacyl-sn-glycerols.

EXAMPLE 2

*Euonymus* Biochemistry

A. Endogenous Lipids and Seed Development

Flowering of *Euonymus alata* occurs in late May, but the onset of the seed maturation phase is delayed until August. During maturation the seed coat bracts become colored intensely orange. Seed fresh weight, dry weight and lipid accumulation over time is shown in FIG. 1. These accumulations follow a pattern typical for developing oilseeds. The oil content of the seed at maturity was 43%. Most of the lipid deposition occurred in September and during this period approximately 0.24 mg lipid/day/seed was deposited. Since this lipid is mainly 3-acetyl-1,2-diacyl-sn-glycerol (MW of 1,2-dioleoyl-3-acetyl-sn-glycerol is 662), and since at mid-maturation the average seed fresh weight is about 30 mg, this gives an average rate of 3-acetyl-1,2-diacyl-sn-glycerol deposition of approximately 500 nmoles/hr/gfw. This rate of deposition is a useful specific activity against which to judge the degree of contribution of exogenous acetate to the biosynthesis of 3-acetyl-1,2-diacyl-sn-glycerols in vivo, for making pool size estimates, and as a yardstick for in vitro enzyme activity measurements.

The accumulation of lipid classes, as measured by mass of fatty acids per seed over time, is shown in FIG. 2. The dominant lipid is 3-acetyl-1,2-diacyl-sn-glycerol, which constitutes 95% of the total lipids at maturity. This number is in close agreement with the 98% of acetoglycerides in *Euonymus alata* oil reported by Kleiman et al. (1967). A small amount of triacylglycerols, amounting to 1.9% of total lipids, co-accumulates with 3-acetyl-1,2-diacyl-sn-glycerol. 1,2-Diacylglycerols represent an even smaller neutral lipid pool, amounting to 0.9% of the total at maturity. Total polar lipids and phosphatidylcholine, the major polar lipid, reach maximum levels by mid-maturation. TLC data show no endogenous acetyl-DAG or acetyl-PC. Their presence would have lead to a consideration of 3-acetyl-1,2-diacyl-sn-glycerol assembly via acetyl-specific transacylases from these novel lipids to 1,2-diacylglycerols.

A range of *Euonymus alata* tissues were harvested and analyzed for total fatty acid content, and for long-chain and acetyl triacylglycerol content by high temperature GC with the appropriate internal standards. The data are shown in FIG. 3. The lipids in embryos and endosperm, separated by dissection from seeds, were dominated by AcTAG, with only a small amount of TAG in the embryo and a very small amount of TAG in the endosperm. In all the other tissues, TAG was only a small or very small percentage of total lipids, and in all other tissues no AcTAG was detected. Thus the acetyl glyceride phenotype is seed-specific.

B. Characterization of Lipid Products from In Vivo Labeling of Halved Seeds with [$^{14}$C]Acetate and Other Substrates Labeled acetate is readily incorporated into heptane-soluble products by developing seeds of *Euonymus alata*. The three major labeled lipids from [$^{14}$C] acetate were 3-acetyl-1,2-diacyl-sn-glycerols (up to 36%), phosphatidylcholine (up to 23%) and 1,2-diacylglycerols (up to 19%). Triacylglycerols (1–4%), phosphatidylethanolamine (ca. 2%), phosphatidylinositol (ca. 2%) and phosphatidic acid (1–2%) were also labeled. No [$^{14}$C] acetyl-polar lipids were detected. When the [$^{14}$C]3-acetyl-1,2-diacyl-sn-glycerol fraction was purified by preparative normal phase TLC, and the distribution of label between the acetyl and long-chain acyl groups analyzed, the molecule was found to be highly labeled in the acetyl group relative to the fatty acyl groups. The distribution of this label depends on the age of the tissue and the concentration of acetate used, such that the label in long-chain acyl groups relative to acetyl groups can vary from 1:10 to 2:1. Digestion of labeled 3-acetyl-1,2-diacyl-sn-glycerol with pancreatic lipase and analysis of the resulting products showed that the fatty acids at the sn-1 and sn-2 position had approximately the same specific radioactivity.

Variation of [$^{14}$C]Acetate Labeling of Lipids During Seed Development

The incorporation of acetate into total lipids and fatty acids, and into the various lipid classes over seed maturation, is shown in FIG. 4. There is the expected sharp increase over early maturation phase and subsequent decline in late maturation, when the activities are expressed on a per seed basis. This rise and fall is also seen when the activities are expressed on a gram fresh wt. basis, although the induction and decay phases are not as pronounced. The maximum rate of incorporation into [$^{14}$Cacetyl] 3-acetyl-1,2-diacyl-sn-glycerol and into [$^{14}$C long-chain acyl] 3-acetyl-1,2-diacyl-sn-glycerol occurs at mid-maturation. The accumulation of labeled DAG, which is largely from the endosperm, also peaks at mid-maturation, and, for the six hour assay period, gives a similar level of labeling as [$^{14}$C long-chain acyl] 3-acetyl-1,2-diacyl-sn-glycerol. Over the mid-maturation period (10–60 days), the distribution of label in individual fatty acids remains fairly constant (13–19% 16:0; 7–10% 18:0; 62–70% 18:1; and 5–11% 18:2). During late maturation (day 80–100), labeling of PC and to a lesser extent DAG continues (FIG. 4), whereas the net accumulation of endogenous polar lipids, phosphatidylcholine and DAG peaks at day 50–60 (FIG. 2). The time course defines the period of harvest for mRNA preparation and for enzyme studies.

Time Course for [$^{14}$C]Acetate Labeling of Lipids

The time courses for [$^{14}$C] acetate incorporation into total lipids and into total long-chain fatty acids was linear over a six hour period with no lag phase. The distribution of label in [$^{14}$Cacetyl] and in [$^{14}$Clong-chain acyl] moieties of 3-acetyl-1,2-diacyl-sn-glycerol was measured, and label in both portions also increased in a linear fashion over time. By contrast, labeling of [$^{14}$C long-chain acyl] DAG plateaus by 6 hours, with [$^{14}$C long-chain acyl] TAG labeling increasing over time, and the rate of PC labeling slowly declining. These results demonstrate that the linear labeling of [$^{14}$C long-chain acyl]3-acetyl-1,2-diacyl-sn-glycerol cannot be derived from the [$^{14}$Clong-chain acyl] DAG and PC pools, as they do not demonstrate the kinetic precursor-product relationship expected if the relationship did exist. If these were precursor pools, then the rate of synthesis of the acetyl glycerides product would increase exponentially. Finally, the appearance of labeled fatty acids equally in both the sn-1 and sn-2 positions of [$^{14}$C fatty acyl] 3-acetyl-1,2-diacyl-sn-glycerol is consistent with a model that involves small pools of intermediates.

In summary, the in vivo labeling kinetics observed are consistent with the synthesis of acetyl glycerides via a DAGAT utilizing acetyl-CoA as a substrate. This enzyme activity is referred to below as a diacylglycerol acetyltransferase (AcDAGAT).

[$^{14}$C]Propionate Labeling of Lipids during Seed Development: An Example of a Related Substrate.

Labeled products from incubation of [$^{14}$C] propionate were analyzed by TLC. A band amounting to 4.5% of the total labeled lipids was observed running just ahead of the major mass of 3-acetyl-1,2-diacyl-sn-glycerol. A slight reduction in polarity of the 3-propionyl glyceride relative to the 3-acetyl-glyceride is expected. Reverse-phase TLC shows about 3.5% labeling in the expected region, with the bands one methylene group offset, in the more lipophilic direction, compared to 3-acetyl-1,2-diacyl-sn-glycerol molecular species bands. This is consistent with the structure of the product as propionyl-1,2-diacyl-sn-glycerol. When the [$^{14}$C] 3-propionyl-1,2-diacyl-sn-glycerol fraction was purified by preparative normal phase TLC and the distribution of label between the propionyl and long-chain acyl groups was analyzed by saponification and phenacyl ester derivatization only a labeled band corresponding to the phenacyl propionate standard was observed. Exogenous acetate at optimum concentration (5 mM) gave a maximum rate of incorporation into [$^{14}$Cacetyl]3-acetyl-1,2-diacyl-sn-glycerol of 40 nmoles/hr/g. fresh wt. At the optimum propionate concentration (10 mM) incorporation into [$^{14}$ Cpropionyl]3-propionyl-1,2-diacyl-sn-glycerol reached a maximum rate of about 10 nmoles/hr/g. fresh wt. Thus the maximal rate of propionate incorporation into the sn-3 position of the glycerides is about 25% of that for acetate. It is unclear whether this difference is a result of different rates of uptake and activation of acetate and propionate, or different rates of utilization by the sn-3 acyltransferase. However, the experiment shows that short-chain acyl groups other than acetate is accommodated by the EaDAGAT; that is, propionate is a "related" substrate group.

C. Diacylglycerol Acetyltransferase Activity.

Characterization of Triacylglycerol Products

Incubation of cell free homogenates (CFH) from developing *Euonymus alata* endosperm plus embryo tissues with [$^{14}$C]acetyl-CoA produced labeled lipids. Analysis by normal phase TLC showed a major labeled band that co-eluted with endogenous Ac-TAG. Long-chain TAG elutes ahead of Ac-TAG in this solvent system. When this labeled band was recovered and analyzed by C18 reversed-phase TLC, the radioactivity migrated with the mass bands corresponding to the major Ac-TAG molecular species, namely C16/C18 and C18/C18. When a unique exogenous diacylglycerol, 1,2-dihexanoyl-sn-glycerol, was added to the assays, a novel band appeared that co-chromatographed with the synthetic 3-acetyl-1,2-dihexanoin standard in both normal and reverse phase TLC systems. The migration of the standard was confirmed by GC analysis of recovered fractions from the TLC plates. Acetyldihexanoin is expected to run as a slightly more polar compound than acetyldioleoin on silica TLC, and as a much less hydrophobic compound on C18 reversed-phase TLC. These product analyses demonstrate that acetyl-CoA and 1,2-diacylglycerol are substrates for the synthesis of 3-acetyl-1,2-diacylglycerols by a DAGAT reaction.

Optimization of Activity

DAGAT assays with acetyl-CoA were set up to give linear initial rates. There was no apparent lag phase before label appears in the AcTAG product, indicating that no detectable [$^{14}$C]acetyl-lipid intermediate was formed. The assay is also dependent on the amount of enzyme added. CFH heated in boiling water for 5 minutes is devoid of activity.

The effects of acetyl-CoA and exogenous diacylglycerol concentrations on activity were also examined. Acetyl-CoA showed typical saturation kinetics, with the reaction rate reaching a plateau above 300 μM. A Lineweaver-Burke reciprocal plot gave estimates of $K_m$=100 μM for acetyl-CoA, and $V_{max}$=2.5 nmoles/min/gfw. This value compares favorably to the average rate of 3-acetyl-1,2-diacyl-sn-glycerol deposition of approximately 500 nmoles/hr/gfw noted above, which converts to 8 nmoles/min/gfw. The standard assay acetyl-CoA concentration of 20 μM gives about a 10-fold lower activity than the maximum AcDAGAT activity. AcDAGAT activity is enhanced only moderately by the addition of exogenous sn-1,2-diolein. Over a concentration range of 0.1–1.2 mM, the average enhancement was 30%. Ethanol, which is used as a carrier for exogenous diacylglycerols, has no effect on activity up to 3% v/v in the assay.

Since short- and medium-chain diacylglycerols were reported as good acyl acceptors in (Lc)DAGAT assays with safflower extracts (Ichihara and Noda (1982) Phytochemistry 21:1895–1901), the effect of short chain diacylglycerol 1,2-dihexanoin, in the AcDAGAT assay was examined. This substrate when acetylated gives a product that is readily separated from the endogenous AcTAG by TLC on silica, as described above. At higher concentrations (4–8 mM), 1,2-dihexanoin effectively out-competes the endogenous DAG as the acetyl acceptor. The maximal rates for synthesis with C16/C18 and C18/C18 diacylglycerol substrate are similar to those for C6/C6. This fact indicates that the AcDAGAT can accommodate a fairly wide range of acyl chain lengths in the diacylglycerol acceptor.

Long-chain DAGAT activity was assayed with 16:0-CoA as substrate. Standardization of this assay showed that it had a linear dependence on CFH to 100 μl (1.5 mg protein) and with a linear incorporation rate for at least 30 minutes. DAGAT activities using either palmitoyl-CoA or acetyl-CoA in the same extract at similar concentrations were compared. The activity with acetyl-CoA was consistently higher than the activity with palmitoyl-CoA, by almost two-fold.

EXAMPLE 3

DAGAT Cloning

A *Euonymus* cDNA for DAGAT was obtained via RT-PCR using degenerated primers and subsequently 3' and 5' RACE to define the 3' and 5' cDNA ends. A full length cDNA clone was obtained via RT-PCR using primers based on the sequence of the 3' and 5' RACE products.

A. General Methods

Total RNA from developing *Euonymus* seeds was extracted according to the procedures of Schultz et al. (1994) (Plant Mol. Biol. Rep. 12: 310–316) or Chung et al. (1996) (Mol. Cells 6: 108–111). For all PCR reactions described below, appropriate controls were included, consisting of the PCR reaction with each primer only. *Escherichia coli* strain HB101 was grown at 37° C. in Luria Broth media (Silhavy et al, 1984), supplemented with the appropriate antibiotics for selection of the constructs: ampicillin 100 mg/ml (pYES2CT), kanamycin 50 mg/ml (pE1776), rifampicine 50 mg/ml (pBBPhas). Database searches were done using the BLAST algorithm. DNA sequences and the deduced amino acid sequence were analyzed with the Vector NTI Suite of InforMax.

B. RT-PCR Using Degenerate Primers

An *Arabidopsis* genomic DAGAT sequence (AC003058, putative DAGAT or ACAT) was used to search the GenBank non-redundant database and the top six matches were aligned. Several conserved regions were identified and used as a basis to design degenerated primers. The degeneracy of all primer combinations is less than 500 in each case. Two sets of primers were designed and used first in a pilot PCR experiment with a partial length *Arabidopsis* EST for DAGAT. One pair of primers yielded the expected fragment of 250 bp. Total RNA isolated from *Euonymus* developing seeds was prepared and cDNA made with the oligodT primer. $^{32}$P-labeled primers sets were used for PCR with the cDNA as template. One set of primers (MP1 and MP6) gave a band of the requisite size. This product was purified from a polyacrylamide gel, reamplified with unlabeled primers (MP1 and MP3), gel-purified and cloned into the PCR TopoTA cloning vector (Invitrogen). From 24 colonies, selected for plasmid preparation and analyzed for the size of the insert, 9 had an insert of the correct length. These 7 clones were sequenced (sequencing facility of MSU) from both ends and 2 (JO752C-1 and -2) were found to be identical and to share high sequence similarity with the *Arabidopsis* DAGAT.

C. 3' and 5' RACE

On the basis of the sequence of the positive clone JO752C-1, primers were designed for 3' and 5' RACE (Gibco RACE kit). Following the protocol of the kit for 3' RACE, cDNA was prepared from total RNA of *Euonymus* seeds using a modified oligodT primer AP (from the kit). A first PCR with primer AUAP (from the kit) and gene specific primer (MP10, 11) was carried out, using the cDNA as template, followed by a second PCR with AUAP and nested gene specific primer MP16. For 5' RACE, a fresh preparation of *Euonymus* seeds total RNA was prepared, DNAase treated and column purified (Qiagen). cDNA was prepared from total RNA of *Euonymus* seeds using a gene specific primer (MP30). The cDNA was C-tailed at the 5' end and nested gene specific primers (MP15 and MP31) in combination with the AAP and AUAP primers were subsequently used to amplify the fragment. Several 3' and 5' RT-PCR fragments were obtained and via southern blot analysis, using the insert of the clone JO752C-1 as a probe, positive hybridizing bands were identified for both 3' and 5' products. These fragments were purified from the gel and cloned into the PCR TopoTA cloning vector. Colonies carrying the vector with the correct insert were selected via colony PCR, using the gene specific primers MP10 and MP31. Sequence analysis of these positive clones revealed that DAGAT sequences had been isolated.

D. Full Length *Euonymus* DAGAT cDNA

On the basis of the sequence of the 3' and 5' RACE products, primers were designed for the 3' and 5' cDNA ends (DAGF and DAGR).

| Primer name | Primer sequence |
|---|---|
| Mp1 | TAY TTY ATG KT5 GCN CCN AC (SEQ ID NO:3) |
| Mp2 | TTY TAY ARR GAY TGG TGG (SEQ ID NO:4) |
| Mp3 | CCA CCA RTC YYT RTA RAA (SEQ ID NO:5) |
| Mp4 | ATG CCN GTI CAY AAR TGG (SEQ ID NO:6) |
| Mp5 | CCA YTT RTC IAC NGG CAT (SEQ ID NO:7) |
| Mp6 | YTC RTG RAA 5AC NGC NGA (SEQ ID NO:8) |
| Mp10 | TAC CCC ATA TGT TCG CAA GG (SEQ ID NO:9) |
| Mp11 | ATG CCA TTG AGA GAG TTT TG (SEQ ID NO:10) |
| Mp16 | TGG TTC YGC ATG TTC TAC TG (SEQ ID NO:11) |
| Mp30 | CAG TCC TTG TAG AAC TCA CGA (SEQ ID NO:12) |
| Mp31 | CTC TCT CAA TGG CAT ACA AAA AG (SEQ ID NO:13) |
| Mp15 | GCA GTA GAA CAT GCA GAA CC (SEQ ID NO:14) |
| DAGF | ATA TGG ATC CAA TAA TGT CTA TGG CTG CTA ACT TGA ACG AAG (SEQ ID NO:15) |
| DAGR | ATA TCT CGA GCA CAA AAC TTG CCT CTA CTC CA (SEQ ID NO:16) |

cDNA was first prepared from total RNA of *Euonymus* seeds, using the oligodT primer (Gibco Superscript Kit). With this cDNA as template, the 3' and 5' primers, and a high fidelity polymerase (pwo from Roche), a full length cDNA PCR product of correct size was obtained, cloned immediately into the BamH1/XhoI site of the yeast vector pYES2CT (Invitrogen), and the sequence of the insert analyzed from both directions. The cDNA nucleotide sequence and encoded amino acid sequence are shown in FIGS. 5 and 6.

A comparison of the amino acid sequence of DAGAT identified in *Euonymus* seed tissue with amino acid sequences of DAGATs from other plants is shown in FIG. 7.

The deduced amino acid sequence is highly similar to all DAGAT proteins described so far for plants (50.7% identity; 91% similarity). The region of the *Euonymus* AcDAGAT protein which is most different from the other DAGAT proteins is the N-terminal end (93 amino acids). Other regions with differences include amino acids 158–200 and 243–268. Predicted transmembrane regions (of which there are about 9 or 10), a putative acyl-binding site, and a putative active site are described by Jako et al. (2001) Plant Phys 126, 861–874); the putative acyl-binding site and putative active site are shown by underlining in FIG. 7.

EXAMPLE 4

Analysis of Yeast Transformed with the Full Length *Euonymus* DAGAT cDNA

The *Euonymus* DAGAT cDNA was cloned into the yeast vector pYES2CT and expressed in the yeast strain *Saccharomyces cerevisiae* strain INVSc1. Two controls were used in subsequent expression analysis. One was the yeast transformed with the empty vector pYES2CT. The second was yeast transformed with the *Arabidopsis* DAGAT cDNA cloned into pYES2CT. All 3 strains were grown in minimal SC-medium lacking uracil supplemented with raffinose and galactose (for induction of the promoter driving the DAGAT expression) as well as acetate at 5 mM final concentration. Cell growth was carefully monitored and cells were harvested at beginning stationary phase, washed and used as described below or the pellets stored at −80° C.

A. Yeast Expression: Lipid Analysis

Methods

Three yeast colonies for each construct were grown in liquid medium and analyzed for lipid content. For growth-phase dependent analysis, a small 3 ml culture of each colony was started in SC-medium with 2% glucose and grown overnight. This culture was diluted 1 to 100 in a volume of 5 ml and grown overnight in SC-medium with 2% glucose until OD of 1 was obtained. This culture was subsequently centrifuged and washed with sterile water, and recovered cells resuspended in 400 ml SC-medium supplemented with galactose and raffinose, with a starting OD of 0.4. Growth was followed over time and 40 ml samples were taken at early and mid exponential phase, and at beginning, mid, and late stationary phase. These samples were washed, pelleted and stored at −4° C. and analyzed as described in the lipid analysis methods. For higher production of lipids, as well as quantitative analysis of the lipid classes, 800 ml yeast cultures of *S. cerevisiae* transformed with either pYES2CT, pYES2CTEaDagat or pYES2CTAtDagat were grown until start of stationary phase and treated as described above.

Lipids were extracted from the yeast pellets by resuspending the pellets in hot isopropanol and then breaking the cells with glass beads. The lipids were extracted with hexane-isopropanol as described by Hara and Radin (1978). The lipid extract included triheptadecanoin and acetyldipentadecanoin as internal standards. The lipids were hydrogenated using Adams catalyst (platinum(IV) oxide) and hydrogen with hexane as solvent. The saturated long-chain triacylglycerols (LcTAG) and sn-3-acetyltriacylgycerols (AcTAG) were separated by preparative TLC, then analyzed by high temperature GC and GC-MS (DB-5ht column).

Results

The total lipids of the transformed yeast strain carrying the pYES2CT vector (negative control) showed the expected pattern of phospholipids, diacylglycerols, sterols, free fatty acids, triacylglycerols and sterol esters. Yeast cells produce a significant amount of LCTAG, which are most evident during the stationary phase (Dahlqvist et al, 2000). The occurrence of acetyl-TAG has not been reported in yeast. Since TAG synthesis is reported to be a function of growth phase, the lipid fraction of transformed yeast cells grown over time was tested, from early logarithmic to late stationary phase. Indeed, endogenous TAG deposition starts at beginning stationary phase. Total lipids were isolated from cultures carrying either the empty vector, the pYES2EaDagat clone (DAGAT of *Euonymus*), or the pYES2AtDagat clone (DAGAT of *Arabidopsis thaliana*), and analyzed by TLC (with iodine staining to visualize unsaturated lipids) and after hydrogenated and preparative TLC by high temperature GC.

The pYES2EaDagat clone (DAGAT of *Euonymus*), when expressed in yeast, increased production of LcTAG 5-fold compared to the vector control. This result shows that the isolated EADAGAT gene can function as a long-chain DAGAT. AcTAG was present at 0.26% of the amount of LcTAG. The maximal deposition of LcTAG and AcTAG were observed at the onset of stationary phase. The AtDAGAT clone, when expressed in yeast, increased production of TAG 20-fold and, in addition, a small amount of AcTAG was found: AcTAG was present at 0.09% of the amount of LcTAG. Thus, the production of AcTAG by the *Arabidopsis* DAGAT in yeast in vivo shows that AcTAG production is not unique for *Euonymus*. The EaDAGAT, however, shows an increased propensity to synthesize AcTAG (about 3-fold) when compared to AtDAGAT; this increased propensity to synthesize AcTAG is referred to as increased specificity for acetyl-CoA as a substrate. The addition of acetate into the yeast culture had only a small effect on the synthesis of the TAG or AcTAG.

The data in the table below summarizes the analytical data above.

| Yeast Line | pYES2CT | pYES2EaDagat | pYES2AtDagat |
|---|---|---|---|
| Total Lipid (mg) | 13.8 | 29.0 | 46.3 |
| Total Fatty Acid (mg) | 5.4 | 14.8 | 34.5 |
| Total TAG (mg) | 1.495 | 7.75 | 30.1 |
| Total AcTAG (mg) | nd | 0.0204 | 0.0281 |

The lipid mass is measured for each sample, which is the cells harvested from 800 ml of culture at 45 hours after inoculation. Cell densities were approximately equal.

The hydrogenated AcTAG enriched fraction isolated by TLC was analyzed by GC. Three molecular species of AcTAG were identified, namely C2C16C16 (22.56 min), C2C16C18 (24.41 min), and C2C18C18 (26.17 min). The retention times corresponded to synthetic standards. Yeast lipids contain predominantly 16:0, 16:1, 18:0 and 18:1 fatty acids, so these hydrogenated species are expected. The C16C18 peak from the GC analysis was analyzed by mass spectroscopy. From interpretation of the diagnostic ions at 239, 267, 355 and 383 in the mass spectrum, the structure is unambiguously acetyl-palmitoylstearoylglycerol.

B. Yeast Expression: In Vitro

Methods

Microsomal fractions were prepared from yeast expressing the empty vector, the *Euonymus* DAGAT (EaDAGAT) vector, and the *Arabidopsis* DAGAT (AtDAGAT) vector, using a protocol modified from that of Dahlqvist et al. (2000) (Proc. Natl. Acad. Sci. USA 97, 6487–6492). 100 ml cultures of yeast grown to beginning stationary phase were centrifuged (~0.5 g of yeast pellet) and the yeast pellet was resuspended in 4 ml of ice-cold buffer (Tris pH 7.9 20 mM, MgCl2 10 mM, EDTA 1 mM, glycerol 5%, DTT 1 mM, ammonium sulfate 0.3 M) and vortexed with 2 ml glass beads for 5 minutes. The suspension was centrifuged at 1,500 g for 15 min at 6° C. The supernatant was subsequently centrifuged at 100,000 g for 1.5 hours at 6° C., and the resulting pellet was resuspended in cold 100 mM potassium phosphate (pH 7.2) and aliquots stored at −80° C. (Ac)DAGAT assays were carried out with $^{14}$C-labeled acetyl-CoA or oleoyl-CoA. Assays contained 100–250 nCi of labeled substrate plus 2–5 μl of microsomes (equivalent to about 5–15 μg of protein), in 50 mM potassium phosphate buffer pH 7.2 and a total volume of 100 μl. The reaction was carried out at 30° C. for 15 minutes. The reaction mix was immediately quenched in hot isopropanol and lipids were extracted and analyzed by TLC as described in Example 1.

Results

The labeled products of DAGAT assays were analyzed by TLC. When [$^{14}$C]oleoyl-CoA was used as a substrate, a significant increase of labeled LcTAG over the amount present in the control (empty vector pYES2) was observed for both EaDAGAT and AtDAGAT. In addition, incubation with [$^{14}$C]acetylCoA resulted in detection of a significant amount of labeled AcTAG in microsomes from yeast expressing the EaDAGAT gene. However, only a very small amount of labeled AcTAG was observed in microsomes from yeast expressing the AtDAGAT gene, and no labeled AcTAG was observed in the control yeast. The [$^{14}$C]AcTAG produced by the microsomes from yeast expressing EaDAGAT was first identified by normal-phase TLC, where it co-eluted with the unlabeled AcTAG. This putative [$^{14}$C] AcTAG band was recovered and re-analyzed by C18 reverse-phase TLC, which showed three bands which could be identified as the molecular species of AcTAG as follows: 16:1/16:1, 16:0/16:1, and 16:1/18:1 in the top band, 16:0/16:1, and 16:1/18:1 in the middle band, and 16:0/18:1, 16:1/18:0, and 18:1/18:1 in the bottom band. The recovered putative [$^{14}$C]AcTAG band was also analyzed by silver nitrate TLC, which showed the label to elute with monoenoic and dienoic AcTAG standards, as expected. These TLC analyses confirm the product as [$^{14}$Cacetyl] AcTAG.

Subsequent assays with yeast microsomes gave the following enzyme activities, using either 50 μM oleoyl-CoA or 45 μM acetyl-CoA as the substrate:

| Yeast Line | pYES2CT | pYES2EaDagat | pYES2AtDagat |
|---|---|---|---|
| Oleoyl-CoA Substrate | 0.18 | 0.22 | 0.11 |
| Acetyl-CoA Substrate | <0.01 | 0.275 | <0.01 |

Activities are expressed as nmoles/min/mg microsomal protein.

In summary, expression of the *Euonymus* DAGAT gene in yeast cells and analysis of the lipids produced shows that the gene can function as a long-chain DAGAT producing long-chain TAG. AcTAG is also produced, and relatively more so than with the corresponding *Arabidopsis* DAGAT gene. Analysis of enzyme activity found in microsomal membrane fractions clearly shows that the *Euonymus* DAGAT has substantial acetyltransferase activity, at least equivalent to the long-chain DAGAT activity, while this acetyltransferase activity is barely detectable (at least a 30-fold reduction) compared with either the endogenous DAGAT activity found in yeast or the activity seen after expressing the *Arabidopsis* gene.

EXAMPLE 5

Analysis of *Arabidopsis* Transformed with the Full Length *Euonymus* DAGAT cDNA Under Control of the Phaseolin Seed-Specific Promoter The *Euonymus* DAGAT cDNA was cloned into the plant expression vector pBBVPhas, at the site of the phaseolin seed-specific promoter. The *Euonymus* DAGAT gene under control of this promoter was expressed in *Arabidopsis thaliana* (var. *Columbia*) to gauge its efficacy to alter oil content and increase the AcTAG content of the oil.

A. Vector Construction and *Arabidopsis* Transformation

The clone pYES2CTPCR5.1 was used as template for PCR using the primers DAGFEapBB (carrying a PstI site) and DAGREaYes (carrying a XhoI site). The 1.5 kbp fragment was cloned (after A-extension) into TopoPCR2.1 to verify the exact sequence and subsequently cloned in the PstI/.XhoI sites of the vector pBBVPhas (Dow Agro Sciences). This vector carries a seed specific phaseolin promoter which is used to express the cloned gene. *Agrobacterium tumefaciens* strain C58C1 was grown at 28° C. in YEP medium, supplemented with the appropriate antibiotics: rifampicine 50 mg/ml, streptomycin 25 mg/ml or gentamycin at a few mg/ml. The constructs (pBBVPhas and pBBVPhas-EaDAGAT) were transferred in *A. tumefasciens* strain C58C1 via electroporation and the presence/absence of the DAGAT sequence verified with whole cell PCR, using DAGAT specific primers.

Six weeks old *Arabidopsis* plants (ecotype Colombia-2) were transformed via vacuum-infiltration method with the *A. tumefasciens* strains, carrying either pBBVPhas or pBBVPhas-EaDAGAT, and the plants grown to maturity. Seeds (T1) were collected and transgenic plants (T1) were selected by germination in soil soaked with BASTA 50 mg/ml final (AgrEvo). The surviving herbicide resistant plants were allowed to grow to maturity, set seed and desiccate. Seed (T2) from a number of single plant lines were harvested. A control for T2 seed analysis was *Arabidopsis* transformed with the empty vector pBBVPhas.

B. T2 Seed Analysis

*Arabidopsis thaliana* (ecotype Colombia-2) mature T2 seeds were collected from the siliques of 6–8 weeks old plants, grown in the growth chambers (16 h light period, 22° C., 80 to 100 μE ligh intensity). Seed from 23 T2 individual plant lines transformed with pBBVPhas-EaDAGAT were harvested, along with seed for 11 control lines (transformed with pBBVPhas). Oil was quantitatively extracted, and TAG and AcTAG analyzed after hydrogenation by high temperature GC using odd-chain internal standards. GC analysis of the AcTAG fraction required prior concentration by TLC to remove overlapping peaks. As a control for analytical variability 8 replicates of a pBBVPhas-EaDAGAT-transformed bulked T2 seed sample were analyzed. Gravimetric oil content determinations were:—

Wild type (Columbia): 35.3%

T2 bulk: 36.9%+0.3%

Vector alone: range=32.35–39.1%, average=35.55%

DAGAT-transformed lines: range 31.45–38.15%, average=35.45%

AcTAG Content Determinations (% in oil) were:—

T2 bulk: 0.036%±0.005%

Vector alone: range=0.007–0.014%, average=0.01±0.002%

DAGAT-transformed lines: range 0.017–0.072%, average=0.036%

The oil content was not enhanced by expressed of the DAGAT, indicating that under these conditions and with this particular line the expression of DAGAT genes is not limiting to oil content. The AcTAG analysis by GC showed a statistically valid increase in AcTAG, which is 2- to 7-fold over wild type.

C. Subsequent Generations of Transformed Plants.

To enhance the AcTAG seed phenotype the pBBVPhas-EaDAGAT-transformed lines are screened at the T2 seedling stage for BASTA herbicide resistance. Lines identified with a 3:1 resistant:susceptible ratio contain a single locus and are used for subsequent generations. Selected single locus lines with the best AcTAG content in their seeds are grown to maturity and T3 mature seed harvested. The lines are identified as homozygous or heterozygous for the transgene by herbicide screening. An approximately 1:2:1 ratio of homozygous:heterozygous:wild type lines are obtained. These are analyzed for total oil content and for AcTAG as described above. The homozygous lines will have higher acetyl glyceride contents.

The homozygous, single locus T3 lines with the highest AcTAG contents in their seeds are crossed with *Arabidopsis* lines containing nulls for the endogenous DAGAT gene, generated by transposon tagging, mutagenesis, siRNA or chimeraplasty. The F1 seed is grown to produce F1 plants, which in turn produce selfed F2 seed. F2 lines contain double homozygotes for the null endogenous DAGAT gene and for the heterologous EaDAGAT. Lines from these F2 plants are identified by screening F3 seed for oil content and AcTAG content as described above. The plants that have highest AcTAG content are homozygous for the EaDAGAT gene but do not have a functional endogenous DAGAT gene. The lack of a functional endogenous gene or polypeptide removes the competition from this gene and allows greater expression of the acetyl glyceride phenotype introduced by the acetyltransferase encoding DAGAT gene. The *Arabidopsis* lines containing nulls for the endogenous DAGAT gene, generated by transposon tagging, mutagenesis, siRNA or chimeraplasty are also transformed with the pBBVPhas-EaDAGAT construct as described in Example V, section A above, to generate T1 plants that are heterozygous for the EaDAGAT gene but do not have a functional endogenous DAGAT gene. On selfing T2 plants that are homozygous for the EaDAGAT gene but do not have a functional endogenous DAGAT gene are produced.

EXAMPLE 6

Synthesis of Novel Triglycerides

A. 1,2-diacyl-3-acetins

Yeast cells transformed with *Euonymus* diacylglycerol acetyltransferase (EuDAGAT) as described in Example 4 resulted in the production of triacylglycerol species with 34 and 36 carbon atoms (counting all acyl carbons but not glycerol carbon atoms) containing an acetyl groups. Enzyme assay for DAGAT in microsomes from the transformed yeast showed activity with both long-chain acyl-CoA and acetyl-CoA. Therefore, expression of this gene results in production of unique triacylglycerols in transformed cells. Furthermore the DAGAT was shown to have a wide specificity in respect of its DAG substrate, with high rates of synthesis with long-chain DAG (C34 or C36) and dihexanoin (C12) (as described above), and therefore is contemplated to accommodate a wide range of novel DAG substrates. In fact, in Example 2, section C, the incubation of acetyl-CoA with 1,2-dihexanoin and a cell free extract from *Euonymus* seeds produced acetyldihexanoin, which is a novel 1,2-diacyl-3-acetins.

B. Other Novel Triglycerides

The EaDAGAT gene allows the production of novel triacylglcyerol structures. For example, in the yeast expression experiment, a triacylglycerol species acetyldipalmitolein was produced; this triacylglycerol species has not been previously reported, and is therefore novel. It is contemplated that the use of the EaDAGAT can be used to produce structures such as acetyldiricinolein, acetyldivemolin, or acetyldicaprin; these structures also have not been previously reported, and are therefore novel.

Such compounds can be produced in vitro by incubating a EaDAGAT enzyme with acetyl-CoA and the appropriate DAG substrate (for example, diricinolein or divemolin) under suitable conditions such that the AcTAG products are synthesized. Exemplary suitable conditions are described above for DAGAT assays.

Such compounds can be produced in vivo by transforming a plant in which the appropriate DAG substrate is present with a gene encoding EaDAGAT under control of a suitable promoter (as for example is described in Example 5), such that EaDAGAT is expressed when and where the appropriate DAG substrate is synthesized, resulting in the synthesis of AcTAG.

In addition, transformed or native organisms are contemplated to produce other novel glycerides when the organism contains an acetyltransferase gene and a substrate related to acetyl-CoA is present endogenously or can be generated from a exogenous substrate. An example is the synthesis of propionyl glycerides by seeds of *Euonymus* when provided with a novel related substrate, propionate, as described in Example 2, section B.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

We claim:

1. An isolated nucleic acid sequence encoding a diacylglycerol acetyltransferase, wherein said nucleic acid sequence encodes SEQ ID NO:2 or a protein that is at least 95% identical thereto and which has diacylglycerol acetyltransferase activity.

2. The nucleic acid sequence of claim 1, wherein the diacylglycerol acetyltransferase is from a plant of the genus *Euonymus*.

3. The nucleic acid sequence of claim 2, wherein the plant is a *Euonymus alata* plant.

4. The nucleic acid sequence of claim 3, wherein the nucleic acid sequence comprises SEQ ID NO: 1.

5. The nucleic acid sequence of claim 1 operably linked to a heterologous promoter.

6. A vector comprising the nucleic acid sequence of claim 1.

7. An isolated host cell comprising the vector of claim 6.

8. The isolated host cell of claim 7, wherein said isolated host cell is a plant cell or a microorganism.

9. An isolated nucleic acid sequence encoding a diacylglycerol acetyltransferase, wherein said nucleic acid sequence encodes SEQ ID NO:2 or a protein that is at least 90% identical thereto and which has diacylglycerol acetyltransferase activity, wherein the diacyiglycerol acetyltransferase is from a *Euonymus alata* plant.

10. The nucleic acid sequence of claim 9 operably linked to a heterologous promoter.

11. A vector comprising the nucleic acid sequence of claim 9.

12. An isolated host cell comprising the vector of claim 11.

13. The isolated host cell of claim 12 wherein said isolated host cell is a plant cell or a microorganism.

* * * * *

SEQUENCE LISTING

```
<160> NUMBER OF SEQ ID NOS: 20

<210> SEQ ID NO 1
<211> LENGTH: 1524
<212> TYPE: DNA
<213> ORGANISM: Euonymus alatus

<400> SEQUENCE: 1

atggctgcta acttgaacga agcctcggat cttaattttt cgcttcggag gagaactggt      60

ggcatctcaa gtacgactgt gcctgattct agttccgaga caagttcgtc ggaggcggac     120

tatttggacg gaggcaaagg tgccgcggac gtcaaagatc gtggggatgg tgcggtggag     180
```

-continued

```
tttcagaatt cgatgaagaa cgtggagagg attgagaaac atgagagccg agtaggattg    240

gattcgagat tcacgtatag gccatcggtc ccggctcatc gcacaataaa ggagagcccg    300

cttagctcgg acgcaatatt caaacagagt cacgcaggtc tcttcaatct ctgtatagta    360

gttctggttg ctgtgaacag caggctgatc attgaaaatc taatgaagta tggatggtta    420

ataaggagtg ggttttggtt cagctcaaga tcattgagag actggcccct ttttatgtgt    480

tgtctcacac taccagtatt ccctcttgct gcttttctgt ttgagaagtt ggctcaaaaa    540

aatttaatat ctgaacctgt tgttgttttg cttcatatag taaacactac agctgccgtt    600

ttataccctg ttttggtgat tctaaggtgt gattctgcct ttatgtctgg ggttacgttg    660

atgctctttg cttgtattgt gtggttaaag ttggtatctt atgctcatac caactatgat    720

atgagagccc tcaccaagtc tgttgaaaag ggggacacgc cgttgagctc tcagaacatg    780

gattactcgt ttgatgtcaa tatcaagagt ttggcatatt ttatggttgc tcccacatta    840

tgttaccaga ttagctatcc tcgtacccca tatgttcgca agggttgggt ggttcgtcaa    900

tttgtcaagt taataatatt tactggactt atgggattta taattgaaca atatatcaat    960

cctattgtcc agaattcaca acaccctttg aaaggaaact tttgtatgc  cattgagaga   1020

gttttgaagc tttcagtccc aaacctttat gtttggctct gcatgttcta ctgccttttt   1080

catctctggt taaacatact tgctgaactt ctttgttttg gtgatcgtga gttctacaag   1140

gattggtgga acgctaaaac tgttgaggag tactggagaa tgtggaacat gcctgttcat   1200

aagtggatgg ttcgtcatat ctacttccca tgcttgagga acgggatacc caagggtgtt   1260

gcttttgtca tttccttctt agtttctgcc gtcttccatg agctatgcat tgctgttccc   1320

tgccacatct tcaagttatg ggctttcttt ggaataatgc ttcaggttcc cttggtgttg   1380

atcacaagtt atctgcaaaa taagttcaga agctcaatgg tgggaaatat gatgttttgg   1440

ttctctttct gcatttttgg tcaacctatg tgcttacttc tatattacca tgatttgatg   1500

aatcgcaatg ggaagatgga gtag                                           1524
```

```
<210> SEQ ID NO 2
<211> LENGTH: 507
<212> TYPE: PRT
<213> ORGANISM: Euonymus alatus

<400> SEQUENCE: 2

Met Ala Asn Asn Leu Asn Glu Ala Ser Asp Leu Asn Phe Ser Leu Arg
1               5                   10                  15

Arg Arg Thr Gly Gly Ile Ser Ser Thr Thr Val Pro Asp Ser Ser Ser
            20                  25                  30

Glu Thr Ser Ser Ser Glu Ala Asp Tyr Leu Asp Gly Gly Lys Gly Ala
        35                  40                  45

Ala Asp Val Lys Asp Arg Gly Asp Gly Ala Val Glu Phe Gln Asn Ser
    50                  55                  60

Met Lys Asn Val Glu Arg Ile Glu Lys His Glu Ser Arg Val Gly Leu
65                  70                  75                  80

Asp Ser Arg Phe Thr Tyr Arg Pro Ser Val Pro Ala His Arg Thr Ile
                85                  90                  95

Lys Glu Ser Pro Leu Ser Ser Asp Ala Ile Phe Lys Gln Ser His Ala
            100                 105                 110

Gly Leu Phe Asn Leu Cys Ile Val Val Leu Val Ala Val Asn Ser Arg
        115                 120                 125
```

-continued

```
Leu Ile Ile Glu Asn Leu Met Lys Tyr Gly Trp Leu Ile Arg Ser Gly
    130                 135                 140

Phe Trp Phe Ser Ser Arg Ser Leu Arg Asp Trp Pro Leu Phe Met Cys
145                 150                 155                 160

Cys Leu Thr Leu Pro Val Phe Pro Leu Ala Ala Phe Leu Phe Glu Lys
                165                 170                 175

Leu Ala Gln Lys Asn Leu Ile Ser Glu Pro Val Val Val Leu Leu His
            180                 185                 190

Ile Val Asn Thr Thr Ala Ala Val Leu Tyr Pro Val Leu Val Ile Leu
        195                 200                 205

Arg Cys Asp Ser Ala Phe Met Ser Gly Val Thr Leu Met Leu Phe Ala
    210                 215                 220

Cys Ile Val Trp Leu Lys Leu Val Ser Tyr Ala His Thr Asn Tyr Asp
225                 230                 235                 240

Met Arg Ala Leu Thr Lys Ser Val Glu Lys Gly Asp Thr Pro Leu Ser
                245                 250                 255

Ser Gln Asn Met Asp Tyr Ser Phe Asp Val Asn Ile Lys Ser Leu Ala
            260                 265                 270

Tyr Phe Met Val Ala Pro Thr Leu Cys Tyr Gln Ile Ser Tyr Pro Arg
        275                 280                 285

Thr Pro Tyr Val Arg Lys Gly Trp Val Val Arg Gln Phe Val Lys Leu
    290                 295                 300

Ile Ile Phe Thr Gly Leu Met Gly Phe Ile Ile Glu Gln Tyr Ile Asn
305                 310                 315                 320

Pro Ile Val Gln Asn Ser Gln His Pro Leu Lys Gly Asn Phe Leu Tyr
                325                 330                 335

Ala Ile Glu Arg Val Leu Lys Leu Ser Val Pro Asn Leu Tyr Val Trp
            340                 345                 350

Leu Cys Met Phe Tyr Cys Leu Phe His Leu Trp Leu Asn Ile Leu Ala
        355                 360                 365

Glu Leu Leu Cys Phe Gly Asp Arg Glu Phe Tyr Lys Asp Trp Trp Asn
    370                 375                 380

Ala Lys Thr Val Glu Glu Tyr Trp Arg Met Trp Asn Met Pro Val His
385                 390                 395                 400

Lys Trp Met Val Arg His Ile Tyr Phe Pro Cys Leu Arg Asn Gly Ile
                405                 410                 415

Pro Lys Gly Val Ala Phe Val Ile Ser Phe Leu Val Ser Ala Val Phe
            420                 425                 430

His Glu Leu Cys Ile Ala Val Pro Cys His Ile Phe Lys Leu Trp Ala
        435                 440                 445

Phe Phe Gly Ile Met Leu Gln Val Pro Leu Val Leu Ile Thr Ser Tyr
    450                 455                 460

Leu Gln Asn Lys Phe Arg Ser Ser Met Val Gly Asn Met Met Phe Trp
465                 470                 475                 480

Phe Ser Phe Cys Ile Phe Gly Gln Pro Met Cys Leu Leu Leu Tyr Tyr
                485                 490                 495

His Asp Leu Met Asn Arg Asn Gly Lys Met Glu
            500                 505
```

<210> SEQ ID NO 3
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 3
tayttyatgk tngcnccnac 20

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
ttytayarrg aytggtgg 18

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
ccaccartcy ytrtaraa 18

<210> SEQ ID NO 6
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: inosine

<400> SEQUENCE: 6
atgccngtnc ayaartgg 18

<210> SEQ ID NO 7
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: inosine
<220> FEATURE:
<221> NAME/KEY: misc_feature
<222> LOCATION: (13)..(13)
<223> OTHER INFORMATION: n is a, c, g, or t

```
<400> SEQUENCE: 7

ccayttrtcn acnggcat                                                   18


<210> SEQ ID NO 8
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 8

ytcrtgraan acngcnga                                                   18


<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9

taccccatat gttcgcaagg                                                 20


<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10

atgccattga gagagttttg                                                 20


<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11

tggttcygca tgttctactg                                                 20


<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12

cagtccttgt agaactcacg a                                               21
```

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
ctctctcaat ggcatacaaa aag 23

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gcagtagaac atgcagaacc 20

<210> SEQ ID NO 15
<211> LENGTH: 42
<212> TYPE: DNA
<213> ORGANISM: Artificial Sequence
<220> FEATURE:
<223> OTHER INFORMATION: Synthetic

<400> SEQUENCE: 15
atatggatcc aataatgtct atggctgcta acttgaacga ag 42

<210> SEQ ID NO 16
<211> LENGTH: 32
<212> TYPE: DNA
<213> ORGANISM: Artificial Sequence
<220> FEATURE:
<223> OTHER INFORMATION: Synthetic

<400> SEQUENCE: 16
atatctcgag cacaaaactt gcctctactc ca 32

<210> SEQ ID NO 17
<211> LENGTH: 507
<212> TYPE: PRT
<213> ORGANISM: Euonymus alatus

<400> SEQUENCE: 17

```
Met Ala Ala Asn Leu Asn Glu Ala Ser Asp Leu Asn Phe Ser Leu Arg
1               5                   10                  15

Arg Arg Thr Gly Gly Ile Ser Ser Thr Thr Val Pro Asp Ser Ser Ser
            20                  25                  30

Glu Thr Ser Ser Ser Glu Ala Asp Tyr Leu Asp Gly Gly Lys Gly Ala
        35                  40                  45

Ala Asp Val Lys Asp Arg Gly Asp Gly Ala Val Glu Phe Gln Asn Ser
    50                  55                  60

Met Lys Asn Val Glu Arg Ile Glu Lys His Glu Ser Arg Val Gly Leu
65                  70                  75                  80

Asp Ser Arg Phe Thr Tyr Arg Pro Ser Val Pro Ala His Arg Thr Ile
                85                  90                  95

Lys Glu Ser Pro Leu Ser Ser Asp Ala Ile Phe Lys Gln Ser His Ala
            100                 105                 110

Gly Leu Phe Asn Leu Cys Ile Val Val Leu Val Ala Val Asn Ser Arg
        115                 120                 125
```

-continued

```
Leu Ile Ile Glu Asn Leu Met Lys Tyr Gly Trp Leu Ile Arg Ser Gly
    130                 135                 140

Phe Trp Phe Ser Ser Arg Ser Leu Arg Asp Trp Pro Leu Phe Met Cys
145                 150                 155                 160

Cys Leu Thr Leu Pro Val Phe Pro Leu Ala Ala Phe Leu Phe Glu Lys
                165                 170                 175

Leu Ala Gln Lys Asn Leu Ile Ser Glu Pro Val Val Val Leu Leu His
            180                 185                 190

Ile Val Asn Thr Thr Ala Ala Val Leu Tyr Pro Val Leu Val Ile Leu
        195                 200                 205

Arg Cys Asp Ser Ala Phe Met Ser Gly Val Thr Leu Met Leu Phe Ala
    210                 215                 220

Cys Ile Val Trp Leu Lys Leu Val Ser Tyr Ala His Thr Asn Tyr Asp
225                 230                 235                 240

Met Arg Ala Leu Thr Lys Ser Val Glu Lys Gly Asp Thr Pro Leu Ser
                245                 250                 255

Ser Gln Asn Met Asp Tyr Ser Phe Asp Val Asn Ile Lys Ser Leu Ala
            260                 265                 270

Tyr Phe Met Val Ala Pro Thr Leu Cys Tyr Gln Ile Ser Tyr Pro Arg
        275                 280                 285

Thr Pro Tyr Val Arg Lys Gly Trp Val Val Arg Gln Phe Val Lys Leu
    290                 295                 300

Ile Ile Phe Thr Gly Leu Met Gly Phe Ile Ile Glu Gln Tyr Ile Asn
305                 310                 315                 320

Pro Ile Val Gln Asn Ser Gln His Pro Leu Lys Gly Asn Phe Leu Tyr
                325                 330                 335

Ala Ile Glu Arg Val Leu Lys Leu Ser Val Pro Asn Leu Tyr Val Trp
            340                 345                 350

Leu Cys Met Phe Tyr Cys Leu Phe His Leu Trp Leu Asn Ile Leu Ala
        355                 360                 365

Glu Leu Leu Cys Phe Gly Asp Arg Glu Phe Tyr Lys Asp Trp Trp Asn
    370                 375                 380

Ala Lys Thr Val Glu Glu Tyr Trp Arg Met Trp Asn Met Pro Val His
385                 390                 395                 400

Lys Trp Met Val Arg His Ile Tyr Phe Pro Cys Leu Arg Asn Gly Ile
                405                 410                 415

Pro Lys Gly Val Ala Phe Val Ile Ser Phe Leu Val Ser Ala Val Phe
            420                 425                 430

His Glu Leu Cys Ile Ala Val Pro Cys His Ile Phe Lys Leu Trp Ala
        435                 440                 445

Phe Phe Gly Ile Met Leu Gln Val Pro Leu Val Leu Ile Thr Ser Tyr
    450                 455                 460

Leu Gln Asn Lys Phe Arg Ser Ser Met Val Gly Asn Met Met Phe Trp
465                 470                 475                 480

Phe Ser Phe Cys Ile Phe Gly Gln Pro Met Cys Leu Leu Leu Tyr Tyr
                485                 490                 495

His Asp Leu Met Asn Arg Asn Gly Lys Met Glu
            500                 505
```

<210> SEQ ID NO 18
<211> LENGTH: 520
<212> TYPE: PRT
<213> ORGANISM: Arabidopsis thaliana

<400> SEQUENCE: 18

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
            260                 265                 270

Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
    290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
            340                 345                 350

Glu Arg Val Leu Lys Leu Ser Val Pro Asn Leu Tyr Val Trp Leu Cys
        355                 360                 365

Met Phe Tyr Cys Phe Phe His Leu Trp Leu Asn Ile Leu Ala Glu Leu
    370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415
```

-continued

```
Met Val Arg His Ile Tyr Phe Pro Cys Leu Arg Ser Lys Ile Pro Lys
            420                 425                 430

Thr Leu Ala Ile Ile Ile Ala Phe Leu Val Ser Ala Val Phe His Glu
        435                 440                 445

Leu Cys Ile Ala Val Pro Cys Arg Leu Phe Lys Leu Trp Ala Phe Leu
    450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
        515                 520


<210> SEQ ID NO 19
<211> LENGTH: 532
<212> TYPE: PRT
<213> ORGANISM: Nicotiana tabacum

<400> SEQUENCE: 19

Met Val Ile Met Glu Leu Pro Glu Ser Val Glu Met Thr Thr Thr Thr
1               5                   10                  15

Thr Thr Ser Gly Ile Glu Asn Leu Asn Ser Asp Leu Asn His Ser Val
            20                  25                  30

Arg Arg Arg Arg Gly Ser Asn Gly Phe Glu Ala Ala Ser Ala Ile Asn
        35                  40                  45

Ser Ser Asp Ala Asn Met Ser Glu Asp Arg Arg Asp Val Cys Gly Ser
    50                  55                  60

Gly Ala Gly Leu Glu Thr Val Asn Glu Arg Ser Lys Ser Val Gly Glu
65                  70                  75                  80

Ser Ser Asp Val Ile Arg Lys Glu Asp Asp Arg Asn Asp Asn Val Ala
                85                  90                  95

Asn Gly Glu Glu Ser Lys Ser Thr Glu Thr Thr Thr Thr Pro Phe Lys
            100                 105                 110

Phe Ala Tyr Arg Ala Ser Ala Pro Ala His Arg Arg Ile Lys Glu Ser
        115                 120                 125

Pro Leu Ser Ser Asp Ala Ile Phe Lys Gln Ser His Ala Gly Leu Phe
    130                 135                 140

Asn Leu Cys Val Val Val Leu Ile Ala Val Asn Ser Arg Leu Ile Ile
145                 150                 155                 160

Glu Asn Leu Met Lys Tyr Gly Leu Leu Ile Arg Ala Gly Phe Trp Phe
                165                 170                 175

Ser Ser Lys Ser Leu Arg Asp Trp Pro Leu Leu Met Cys Cys Leu Ser
            180                 185                 190

Leu Gln Ile Leu Pro Leu Ala Ala Phe Leu Val Glu Lys Leu Ala Gln
        195                 200                 205

Gln Arg His Leu Thr Glu Arg Ala Val Val Thr Leu His Ile Thr Ile
    210                 215                 220

Thr Thr Ala Ala Ile Leu Tyr Pro Val Leu Val Ile Leu Gly Cys Asp
225                 230                 235                 240

Ser Ala Phe Leu Phe Gly Val Ile Leu Met Leu Val Ala Cys Ile Val
                245                 250                 255

Trp Met Lys Leu Val Ser Tyr Ala His Thr Asn His Asp Met Arg Gln
            260                 265                 270
```

-continued

```
Leu Ala Lys Ser Thr Asp Lys Asp Glu Thr Ser Asp Gly Asp Phe Ser
        275                 280                 285

Tyr Asp Val Ser Phe Lys Ser Leu Ala Tyr Phe Met Val Ala Pro Thr
    290                 295                 300

Leu Cys Tyr Gln Leu Ser Tyr Pro His Thr Pro Cys Ile Arg Lys Gly
305                 310                 315                 320

Trp Val Ala Arg Gln Phe Ile Lys Leu Val Ile Phe Thr Gly Leu Met
                325                 330                 335

Gly Phe Ile Ile Glu Gln Tyr Ile Asn Pro Ile Val Gln Asn Ser Gln
            340                 345                 350

His Pro Leu Lys Gly Asn Leu Leu Tyr Ala Ile Glu Arg Val Leu Lys
        355                 360                 365

Leu Ser Val Pro Asn Leu Tyr Val Trp Leu Cys Met Phe Tyr Cys Phe
    370                 375                 380

Phe His Leu Trp Leu Asn Ile Leu Ala Glu Leu Leu Cys Phe Gly Asp
385                 390                 395                 400

Arg Glu Phe Tyr Lys Asp Trp Trp Asn Ala Lys Thr Ile Asp Glu Tyr
                405                 410                 415

Trp Arg Met Trp Asn Met Pro Val His Lys Trp Met Val Arg His Ile
            420                 425                 430

Tyr Phe Pro Cys Leu Arg Asn Gly Ile Pro Lys Gly Val Ala Ile Leu
        435                 440                 445

Ile Ala Phe Leu Val Ser Ala Val Phe His Glu Leu Cys Ile Ala Val
    450                 455                 460

Pro Cys Arg Leu Phe Lys Trp Trp Ala Phe Met Gly Ile Met Phe Gln
465                 470                 475                 480

Val Pro Leu Val Ile Leu Thr Asn Phe Leu Gln Asn Lys Phe Gln Ser
                485                 490                 495

Ser Met Val Gly Asn Met Met Phe Trp Cys Phe Phe Cys Ile Leu Gly
            500                 505                 510

Gln Pro Met Cys Val Leu Leu Tyr Tyr His Asp Val Met Asn Arg Lys
        515                 520                 525

Ser Ser Ala Arg
    530


<210> SEQ ID NO 20
<211> LENGTH: 534
<212> TYPE: PRT
<213> ORGANISM: Perilla frutescens

<400> SEQUENCE: 20

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Arg Gln Ser
            20                  25                  30

Ala Arg Ser Val Pro Pro Leu Leu Asp Ser Asp Ser Asn Ser Leu Glu
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110
```

-continued

```
Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
    130                 135                 140

Cys Ile Val Val Leu Val Ala Val Asn Ser Arg Leu Ile Ile Glu Asn
145                 150                 155                 160

Leu Met Lys Tyr Gly Trp Leu Ile Lys Ser Gly Phe Trp Phe Ser Ser
                165                 170                 175

Thr Ser Leu Arg Asp Trp Pro Leu Leu Met Cys Cys Leu Ser Leu Pro
            180                 185                 190

Val Phe Ala Leu Ala Ser Phe Leu Val Glu Lys Leu Val Lys Leu Asn
        195                 200                 205

Tyr Ile Pro Glu Trp Val Ala Val Phe Leu His Val Thr Ile Thr Thr
    210                 215                 220

Val Glu Ile Leu Phe Pro Val Val Val Ile Leu Arg Cys Asp Ser Ala
225                 230                 235                 240

Val Leu Ser Gly Val Thr Leu Met Leu Phe Ala Cys Thr Val Trp Leu
                245                 250                 255

Lys Leu Val Ser Tyr Ala His Thr Asn Tyr Asp Leu Arg Val Leu Ala
            260                 265                 270

Lys Ser Leu Asp Lys Trp Glu Ala Met Ser Arg Tyr Trp Asn Leu Asp
        275                 280                 285

Tyr Ala Tyr Asp Val Ser Phe Lys Ser Leu Ala Tyr Phe Met Val Ala
    290                 295                 300

Pro Thr Leu Cys Tyr Gln Pro Ser Tyr Pro Arg Thr Ala Cys Ile Arg
305                 310                 315                 320

Lys Gly Trp Val Val Arg Gln Leu Ile Lys Leu Val Ile Phe Thr Gly
                325                 330                 335

Leu Met Gly Phe Ile Ile Glu Gln Tyr Ile Asn Pro Ile Val Gln Asn
            340                 345                 350

Ser Gln His Pro Leu Lys Gly Asn Leu Leu Tyr Ala Ile Glu Arg Val
        355                 360                 365

Leu Lys Leu Ser Val Pro Asn Leu Tyr Val Trp Leu Cys Met Phe Tyr
    370                 375                 380

Cys Phe Phe His Leu Trp Leu Asn Ile Leu Ala Glu Leu Leu Cys Phe
385                 390                 395                 400

Gly Asp Arg Glu Phe Tyr Lys Asp Trp Trp Asn Ala Arg Thr Val Glu
                405                 410                 415

Glu Tyr Trp Arg Met Trp Asn Met Pro Val His Lys Trp Met Val Arg
            420                 425                 430

His Ile Tyr Cys Pro Cys Leu Gln Asn Gly Ile Pro Lys Ile Val Ala
        435                 440                 445

Val Leu Ile Ala Phe Leu Val Ser Ala Ile Phe His Glu Leu Cys Val
    450                 455                 460

Ala Val Pro Cys Gln Ile Phe Lys Phe Trp Ala Phe Ser Gly Ile Met
465                 470                 475                 480

Leu Gln Val Pro Leu Val Ile Val Thr Asn Tyr Leu Gln Glu Lys Phe
                485                 490                 495

Lys Asn Ser Met Val Gly Asn Met Met Phe Trp Cys Phe Phe Cys Ile
            500                 505                 510
```

-continued

```
Phe Gly Gln Pro Met Cys Val Leu Leu Tyr Tyr His Asp Leu Met Asn
        515                 520                 525

Arg Lys Ala Ser Ala Arg
    530
```